US012735668B2

(12) United States Patent
Igarashi

(10) Patent No.: US 12,735,668 B2
(45) Date of Patent: Sep. 15, 2026

(54) PRIMING METHOD AND BIOLOGICAL COMPONENT TREATMENT SYSTEM

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1020 days.

(21) Appl. No.: 17/697,590

(22) Filed: Mar. 17, 2022

(65) Prior Publication Data

US 2022/0204910 A1 Jun. 30, 2022

Related U.S. Application Data

(63) Continuation of application No. PCT/JP2020/034923, filed on Sep. 15, 2020.

(30) Foreign Application Priority Data

Sep. 20, 2019 (JP) ................................ 2019-171248

(51) Int. Cl.
*C12M 3/00* (2006.01)
*C12M 1/00* (2006.01)
(Continued)

(52) U.S. Cl.
CPC ............ *C12M 29/20* (2013.01); *C12M 23/20* (2013.01); *C12M 25/12* (2013.01); *C12M 29/16* (2013.01); *C12M 29/18* (2013.01); *C12M 41/48* (2013.01)

(58) Field of Classification Search
CPC .............................. C12M 29/20; C12M 29/16
See application file for complete search history.

(56) References Cited

U.S. PATENT DOCUMENTS 7,387,661 B2 * 6/2008 Wu ........................ B01D 53/22 95/45
2003/0116015 A1 * 6/2003 Sengupta ........... B01D 19/0031 96/6

(Continued)

FOREIGN PATENT DOCUMENTS

CA 2918931 C * 11/2019
DE 102010030238 12/2011

(Continued)

OTHER PUBLICATIONS

English translation of JP 2009297340 to Furuhashi et al., generated 2025.*

(Continued)

*Primary Examiner* — Nathan A Bowers
(74) *Attorney, Agent, or Firm* — Sheridan Ross P.C.

(57) ABSTRACT

A biological component treatment system according to embodiments of the present disclosure includes an IC route through which the liquid is capable of flowing in inner cavities of hollow fibers, and an EC route through which the liquid is capable of flowing in a main space on an outer side of the hollow fibers. The biological component processing system is further equipped with a control unit that controls a flowing state of the liquid through the IC route and the EC route. The control unit, at a time of priming, while the liquid flows through both the IC route and the EC route, causes a differential pressure to be generated between the liquid flowing through the inner cavities and the liquid flowing through the main space, and causes the gas to flow out from the hollow fibers.

20 Claims, 12 Drawing Sheets

(51) Int. Cl.
*C12M 1/12* (2006.01)
*C12M 1/36* (2006.01)

(56) References Cited

U.S. PATENT DOCUMENTS

| | | | | |
|---|---|---|---|---|
| 2005/0203493 | A1* | 9/2005 | Kuroda | A61M 1/3609 606/5 |
| 2009/0233351 | A1* | 9/2009 | Akechi | B01D 71/32 324/693 |
| 2017/0232180 | A1* | 8/2017 | Umeda | B01D 65/00 |
| 2017/0349873 | A1 | 12/2017 | Frank et al. | |
| 2018/0282695 | A1 | 10/2018 | Nankervis et al. | |

FOREIGN PATENT DOCUMENTS

| | | |
|---|---|---|
| EP | 1013295 | 6/2000 |
| JP | 2001-149471 | 6/2001 |
| JP | 2009-297340 | 12/2009 |
| JP | 2017-143775 | 8/2017 |
| JP | 2019-171248 | 10/2019 |
| WO | WO 99/13925 | 3/1999 |

OTHER PUBLICATIONS

International Search Report and Written Opinion for International (PCT) Patent Application No. PCT/JP2020/034923, dated Dec. 16, 2020, 10 pages.

Official Action for European Patent Application No. 18862725.1, dated Feb. 20, 2025, 5 pages.

English Translation of Official Action for Japan Patent Application No. 2022-509030, dated Jul. 30, 2024, 4 pages.

* cited by examiner 12
18
18A
18B
18C
18D
18E
18F
16A
16B
16C
16D
16E
16
16K
16L
58
16J
58
23 (22)
56
54
29
29a
GAS
COMPONENT
29b
40
50
16N
16M
10
16F
16I
16H
28d (28)
24
28c (28)
16G
132
130
136
26
26a
28b (28)
26b
21 (20)
26b
28a (28)
134
15 (14)

10
42
42
60
100
44
60
60
100
48
48
90
48
48
102
80
48
41
100
40
60
60
60
52a
58
70
70
70
52
56
54
70
58
50

12
CELL SOLUTION BAG
CLEANING SOLUTION BAG
CULTURE MEDIUM BAG
WASTE LIQUID BAG
COLLECTION BAG
P
18A
18B
18C
18D
18E
16A
16B
16C
16D
16E
16F
16G
16H
16I
16J
16K
16L
16M
16N
34a (34)
34b (34)
34c (34)
30a (30)
30b (30)
30c (30)
30d (30)
44A1 (44A)
44A2 (44A)
44B1 (44B)
44B2 (44B)
44C
35a (35)
35b (35)
35
36
37
32
40
80
90
100
120
10
21 (20)
28a
28b
28c
28d
29
α
β
γ
δ

23
WASTE LIQUID BAG
18D
44C
35a (35)
35b (35)
136
CONTROL UNIT
44A2
28a
28d
26
24
δ
44B2
30d (30)
28c
30c (30)
28b
29
γ
α
β
44A1
44B1
30a (30)
30b (30)
P
44A
34b
44B
18B
CLEANING SOLUTION BAG 23
44A
44A1
α
44A2
30a (30)
30d (30)
24
26
DRIVING OF PUMP :
DRIVING OF PUMP STOPPED :
CLAMP OPEN :
CLAMP CLOSED :
β
28a
28b
28c
28d
35a (35)
44C
18D
18B
34b
CLEANING SOLUTION BAG
WASTE LIQUID BAG
29
δ
35b (35)
44B2
136
CONTROL UNIT
44B
γ
44B1
30b (30)
30c (30)

23
DRIVING OF PUMP :
DRIVING OF PUMP STOPPED :
CLAMP OPEN :
CLAMP CLOSED :
CLEANING SOLUTION BAG
18B
34b
44A
44B
30a (30)
P
44A1
α
β
30d (30)
44A2
26
24
28a
28b
28c
28d
29
γ
44B1
30b (30)
30c (30)
44B2
δ
35a (35)
35b (35)
44C
WASTE LIQUID BAG
18D
CONTROL UNIT
136

23
44A
44A1
α
44A2
30a (30)
30d (30)
DIFFERENTIAL PRESSURE
24
26
DRIVING OF PUMP :
DRIVING OF PUMP STOPPED :
CLAMP OPEN :
CLAMP CLOSED :
β
28a
28b
28c
28d
35a (35)
44C
18D
18B
34b
CLEANING SOLUTION BAG
WASTE LIQUID BAG
29
δ
35b (35)
44B2
136
CONTROL UNIT
44B
γ
44B1
30b (30)
30c (30)

23A
44A
44A1
α
44A2
30a (30)
30d (30)
DIFFERENTIAL PRESSURE
24
26
DRIVING OF PUMP :
DRIVING OF PUMP STOPPED :
CLAMP OPEN :
CLAMP CLOSED :
β
28a
35a (35)
28b
28c
28d
44C
18B
34b
18D
CLEANING SOLUTION BAG
WASTE LIQUID BAG
29
δ
35b (35)
44B2
136A
CONTROL UNIT
44B
γ
30b (30)
44B1
30c (30)

23B
DRIVING OF PUMP :
DRIVING OF PUMP STOPPED :
CLAMP OPEN :
CLAMP CLOSED :
WASTE LIQUID BAG
18D
44C
35a (35)
35b (35)
136B
CONTROL UNIT
44A2
28a
28d
30d (30)
26
24
δ
44B2
P
28c
DIFFERENTIAL PRESSURE
30c (30)
29
γ
28b
α
β
44A1
44B1
30a (30)
30b (30)
44A
44B
34b
CLEANING SOLUTION BAG
18B

23C
DRIVING OF PUMP :
DRIVING OF PUMP STOPPED :
CLAMP OPEN :
CLAMP CLOSED :
WASTE LIQUID BAG
18D
44C
35a (35)
35b (35)
136C
CONTROL UNIT
44A2
28a
28d
30d (30)
26
24
DIFFERENTIAL PRESSURE
28c
28b
δ
44B2
30c (30)
29
γ
α
β
44A1
44B1
30a (30)
30b (30)
44A
34b
44B
18B
CLEANING SOLUTION BAG

PRIMING METHOD AND BIOLOGICAL COMPONENT TREATMENT SYSTEM

CROSS REFERENCE TO RELATED APPLICATIONS

The present application is a continuation of and claims benefit to PCT Application No. PCT/JP2020/034923 filed on Sep. 15, 2020, entitled "PRIMING METHOD AND BIOLOGICAL COMPONENT TREATMENT SYSTEM" which claims priority to Japanese Patent Application No. 2019-171248 filed on Sep. 20, 2019. The entire disclosures of the applications listed above are hereby incorporated herein by reference, in their entirety, for all that they teach and for all purposes.

BACKGROUND

The present disclosure relates to a priming method and a biological component treatment system in which a liquid is allowed to flow through a treatment unit and a gas in the treatment unit is discharged.

In the practice of regenerative medicine, a treatment is performed in which biological cells (e.g., biological components) are collected and cultured, and the cultured cells are administered to a patient. In a propagation process for culturing cells, for example, as disclosed in Japanese Laid-Open Patent Publication No. 2017-143775, a cell culture system (e.g., a biological component treatment system), in which there is employed a cell culture container (e.g., a treatment unit) having hollow fibers inside a case, is used. In such a biological component treatment system, a liquid containing the cells is supplied to inner cavities (e.g., a lumen) of the hollow fibers to thereby seed the cells on the inner circumferential surfaces of the hollow fibers, and thereafter, a culture medium is delivered to the treatment unit (e.g., on the inside and the outside of the hollow fibers), thereby culturing the cells.

In this type of biological component treatment system, in order to remove air (e.g., gas, etc.) inside the treatment unit including the hollow fibers before propagation of the cells is performed, priming is carried out by allowing a predetermined liquid (e.g., a priming solution such as a saline solution or the like, or alternatively, the culture medium) to flow through the treatment unit. In a conventional priming process, for example, after the liquid has flowed through the inner cavities of the hollow fibers, a process is carried out in which the liquid is made to flow to the outer side of the hollow fibers.

SUMMARY

However, in the treatment unit, in the case that the hollow fibers having a coating formed on the inner circumferential surfaces of the inner cavities are applied to the treatment unit, fluid is likely to accumulate inside a membrane structure that surrounds the inner cavities. Therefore, even if the above-described priming process is performed, a problem arises in that it is difficult for air to be released from the membrane structure.

The present disclosure has been devised in relation to the aforementioned technique, and has the object of providing, for example, a priming method and a biological component treatment system, in which it is possible to easily and reliably discharge a gas from the hollow fibers.

In order to achieve the above-described object, a first aspect of the present disclosure includes a priming method for discharging a gas contained within hollow fibers by introducing a liquid into a treatment unit including the hollow fibers on which a coating is formed on inner circumferential surfaces that constitute inner cavities thereof, and a container having an internal space in which the hollow fibers are accommodated, wherein, in the treatment unit, there are connected an internal route through which the liquid is allowed to flow in the inner cavities, and an external route through which the liquid is allowed to flow in the internal space on an outer side of the hollow fibers, and wherein, at a time of priming, while the liquid flows through both the internal route and the external route, a differential pressure is generated between the liquid flowing through the inner cavities and the liquid flowing through the internal space, and the gas is made to flow out from the hollow fibers.

Further, in order to achieve the above-described object, a second aspect of the present disclosure includes a biological component treatment system including a treatment unit including hollow fibers on which a coating is formed on inner circumferential surfaces that constitute inner cavities thereof, and a container having an internal space in which the hollow fibers are accommodated, the biological component treatment system including an internal route connected to the treatment unit, and through which the liquid is allowed to flow in the inner cavities, an external route connected to the treatment unit, and through which the liquid is allowed to flow in the internal space on an outer side of the hollow fibers, and a control unit configured to control a flowing state of the liquid through the internal route and the external route, wherein the control unit, at a time of priming, while the liquid flows through both the internal route and the external route, causes a differential pressure to be generated between the liquid flowing through the inner cavities and the liquid flowing through the internal space, and causes the gas to flow out from the hollow fibers.

In the above-described priming method and the biological component treatment system, it is possible to easily and reliably discharge a gas from the hollow fibers.

DETAILED DESCRIPTION

Preferred embodiments of the present disclosure will be presented and described in detail below with reference to the accompanying drawings.

Figure 1:
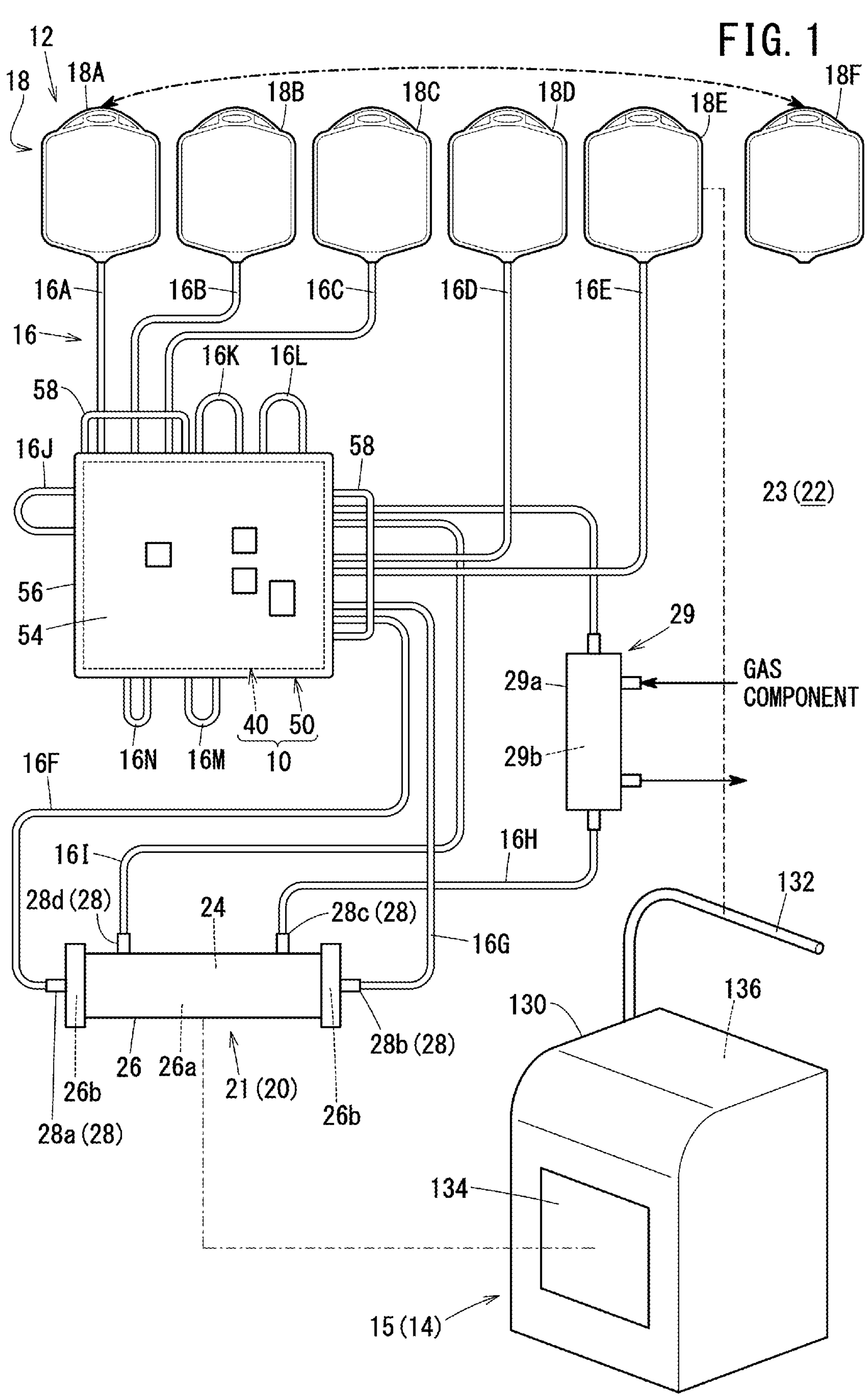
FIG. 1 is an explanatory diagram showing a biological component treatment system to which a biological component cassette and a biological component kit according to embodiments of the present disclosure.

As shown in FIG. 1, a biological component treatment system 22 according to a first embodiment of the present disclosure is equipped with a biological component kit 12 (hereinafter simply referred to as a kit 12) in which a liquid containing a biological component and a liquid for treating the biological component are capable of flowing, and a biological component treatment device 14 in which the kit 12 is set. Further, the kit 12 includes a biological component cassette 10 (hereinafter, simply referred to as a cassette 10) in which a plurality of pathways for the liquids are consolidated, and which is set in the biological component treatment device 14.

The kit 12 comprises, as members that constitute the plurality of pathways, and in addition to the cassette 10, a plurality of tubes 16, a plurality of medical bags 18, and a treatment unit 20. The kit 12 allows a plurality of types of liquids contained in each of the medical bags 18 to flow through the cassette 10 and through each of the tubes 16 under the operation of the biological component treatment device 14, and is constituted so as to obtain a target product by processing the liquids in the treatment unit 20.

The biological component treatment system 22 according to the present embodiment serves to perform a propagation process for propagating biological cells (biological components) in regenerative medicine, and a bioreactor 21 used for propagation of the cells is applied to the treatment unit 20 of the kit 12. Further, as the liquids that flow inside the kit 12, there may be cited a solution containing the cells (hereinafter referred to as a cell solution), a culture medium (culture solution) which is supplied in order to propagate the cells, a cleaning solution for cleaning the interior of the kit 12, and a stripping solution for stripping the cells. More specifically, in a set state of the kit 12, the biological component treatment device 14 carries out a propagation process in which the bioreactor 21 is seeded with the cell solution, and furthermore, the cells are cultured by supplying the culture medium, and thereafter, the propagated cells are stripped and collected from the bioreactor 21. Hereinafter, the biological component treatment device 14 may also be referred to as a cell propagation device 15, and the biological component treatment system 22 may also be referred to as a cell propagation system 23.

The biological cells are not particularly limited, and may include, for example, cells (T cells and the like) contained in blood, and stem cells (ES cells, iPS cells, mesenchymal stem cells, and the like). An appropriate culture medium may be selected according to the biological cells, and for example, as such a culture medium, there may be cited a balanced salt solution (BSS) as a basic solution, and various amino acids, vitamins, serum and the like may be added thereto in order to prepare the culture medium. Further, the cleaning solution is not particularly limited, and as examples thereof, there may be cited buffering solutions such as PBS (Phosphate Buffered Salts), TBS (Tris-Buffered Saline) and the like, or physiological saline. Further, as the stripping solution, for example, trypsin or an EDTA solution can be applied.

Among the plurality of medical bags 18 of the kit 12, there are included a cell solution bag 18A in which the cell solution is accommodated, a cleaning solution bag 18B in which the cleaning solution is accommodated, and a culture medium bag 18C in which the culture medium is accommodated. Furthermore, as the plurality of medical bags 18, the kit 12 includes empty bags, and such empty bags include a waste liquid bag 18D into which a liquid that is discarded in the propagation process flows, and a collection bag 18E in which cells (and other liquids) obtained in the propagation process are collected. Further, among the medical bags 18, a stripping solution bag 18F in which the stripping solution is accommodated is separately prepared. During the course of the propagation process, the stripping solution bag 18F is exchanged by an operator with one of the medical bags 18 (for example, the cell solution bag 18A) that has been connected beforehand.

The cell solution bag 18A, the cleaning solution bag 18B, and the culture medium bag 18C, etc., are aseptically joined to ends of the respective tubes 16 using a non-illustrated aseptic joining device. Alternatively, each of the medical bags 18 may be fixed to ends of the respective tubes 16 in a non-separable manner, and may have a structure for ensuring sterility inside the kit 12. Further, alternatively, the kit 12 may apply a connection structure (not shown) that enables a detachable connection between the tubes 16 and each of the medical bags 18.

Although not particularly limited, for the bioreactor 21 of the kit 12, it is preferable to use a culture medium base material having a large surface area, and in the present embodiment, hollow fibers 24 are applied thereto. More specifically, the bioreactor 21 includes a plurality of the hollow fibers 24 (for example, ten thousand or more hollow fibers), and a cylindrical container 26 having a main space 26*a* (internal space) therein in which the plurality of hollow fibers 24 are accommodated.

Figure 2:
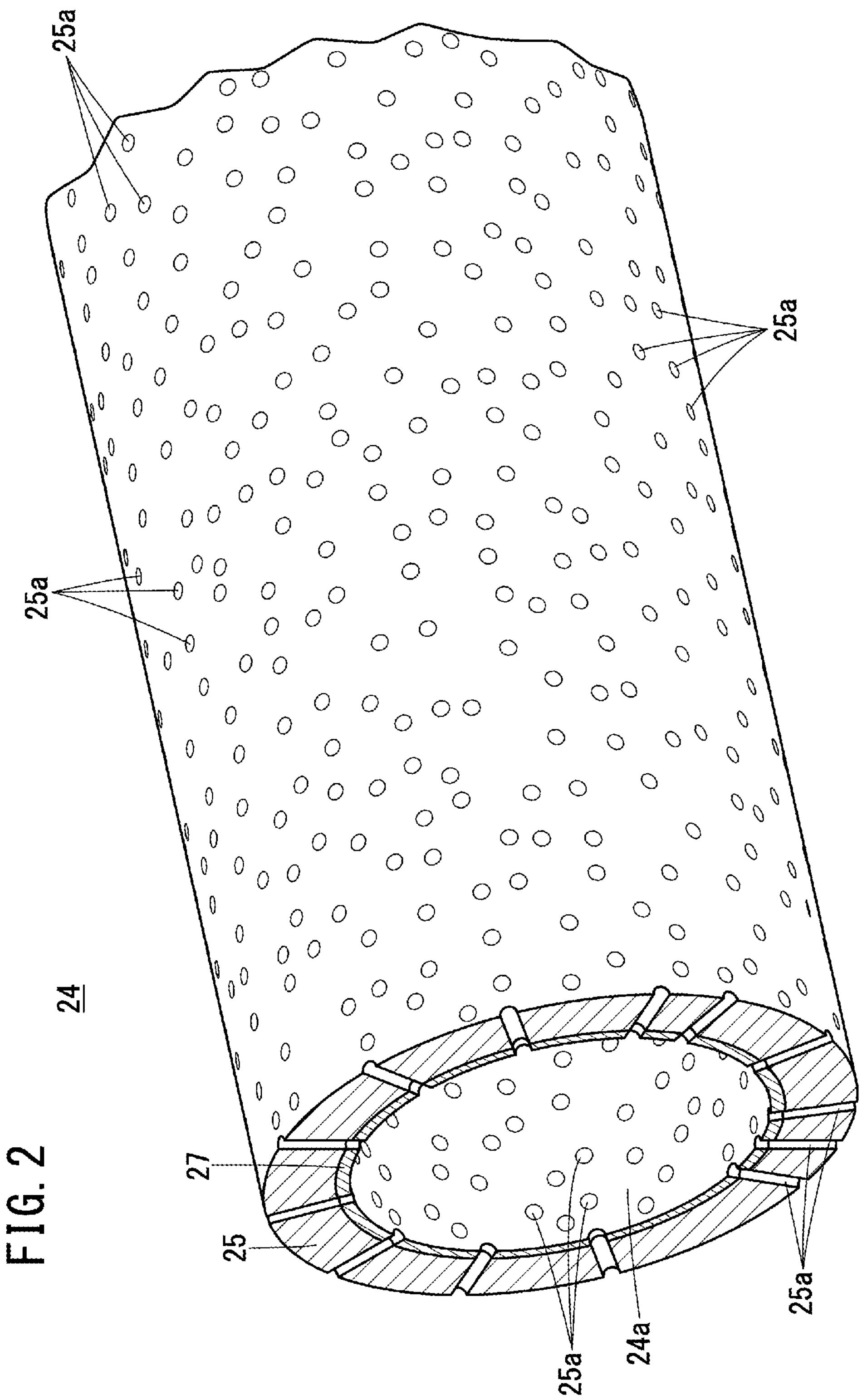
FIG. 2 is a cross-sectional perspective view showing an enlarged structure of a hollow fiber according to embodiments of the present disclosure.

The plurality of hollow fibers 24 are accommodated along an axial direction of the container 26, and both ends thereof are retained by non-illustrated retaining walls of the container 26. As shown in FIG. 2, each of the hollow fibers 24 is formed with constitution in which an inner cavity 24*a* thereof is surrounded by a membrane structure 25 (hollow fiber membrane). The inner cavities 24*a* penetrate through the hollow fibers 24 along the direction in which the hollow fibers 24 extend. The diameters of the inner cavities 24*a*, for example, are formed on the order of approximately 200 micrometers, and communicate with end spaces 26*b* on both axial sides of the retaining walls.

The membrane structure 25 is constituted in the form of a porous body having a large number of pores 25*a* that extend in the thickness direction. The respective pores 25*a* communicate between an outer side (e.g., the main space 26*a*) of the hollow fibers 24 and the inner cavities 24*a*, and are formed with sizes that regulate the passage of cells and proteins, but on the other hand, enable solutions and substances of low molecular weight to pass therethrough. The diameter of the pores 25*a* is set, for example, on the order of 0.005 micrometers to 10 micrometers.

The material constituting the membrane structure 25 of the hollow fibers 24 is not particularly limited, but as examples thereof, there may be cited polyolefin resins such as polypropylene, polyethylene, and the like, and polymer materials such as polysulfone, polyether sulfone, polyacrylonitrile, polytetrafluoroethylene, polystyrene, polymethylmethacrylate, cellulose acetate, cellulose triacetate, regenerated cellulose, and the like.

The respective hollow fibers 24 further include a coating 27 provided on an inner circumferential surface of the membrane structure 25 surrounding the inner cavities 24*a*. The coating 27 has a function of promoting seeding of the cells that are introduced inside the hollow fibers 24, and is coated on the entire inner circumferential surface (or a portion inside the pores 25*a*) of the membrane structure 25. The coating 27 includes a plurality of holes corresponding to the pores 25*a* of the membrane structure 25, and ensures communication between the inner cavities 24*a* of the hollow fibers 24 and an outer side thereof. The material that constitutes the coating 27 is not particularly limited, but as examples thereof, there may be cited fibronectin, laminin, vitronectin, collagen, tenascin, fibrinogen, gelatin, polylysine, and the like.

The above-described hollow fibers 24 supply the culture medium and a predetermined gas component and the like via the pores 25*a* to the cells that are adhered to the coating 27. Hereinafter, in the cell propagation system 23, constitution in which liquid is primarily circulated in the inner cavities 24*a* of the hollow fibers 24 may also be referred to as intracapillary (IC) constitution, and constitution in which liquid is primarily circulated on outer sides of the hollow fibers 24 may also be referred to as extracapillary (EC) constitution.

As shown in FIG. 1, the container 26 has an axial length which is capable of accommodating the respective hollow fibers 24 when the hollow fibers 24 are extended in a substantially linear shape. The container 26 is equipped with four terminals 28 (a first IC terminal 28*a*, a second IC terminal 28*b*, a first EC terminal 28*c*, and a second EC terminal 28*d*) that are connected respectively to the tubes 16. The first IC terminal 28*a* is provided at one end of the container 26 and communicates with the end space 26*b* on one end side. The second IC terminal 28*b* is provided at another end of the container 26 and communicates with the end space 26*b* on another end side. The first EC terminal 28*c* is provided on an outer peripheral surface of the container 26 in the vicinity of the other end side, and communicates with the main space 26*a* at a location in close proximity to the other end. The second EC terminal 28*d* is provided on an outer peripheral surface of the container 26 in the vicinity of the one end side, and communicates with the main space 26*a* at a location in close proximity to the one end.

The bioreactor 21, in a state of being set in the cell propagation device 15, is preferably fixed rotatably by the cell propagation device 15 in a vertical direction (a direction along a vertical plane: heightwise direction), a horizontal direction (a direction along a horizontal plane: widthwise direction), or so as to be capable of rotating about an axis of the container 26. Consequently, it becomes possible to easily guide the air in the interior of the bioreactor 21 to any one of the four terminals 28.

The plurality of tubes 16 of the kit 12 include a cell solution tube 16A connected between the cell solution bag 18A and the cassette 10, a cleaning solution tube 16B connected between the cleaning solution bag 18B and the cassette 10, a culture medium tube 16C connected between the culture medium bag 18C and the cassette 10, a waste liquid tube 16D connected between the waste liquid bag 18D and the cassette 10, a collection tube 16E connected between the collection bag 18E and the cassette 10, a first IC tube 16F connected between the first IC terminal 28*a* of the bioreactor 21 and the cassette 10, a second IC tube 16G connected between the second IC terminal 28*b* of the bioreactor 21 and the cassette 10, a first EC tube 16H connected between the first EC terminal 28*c* of the bioreactor 21 and the cassette 10, and a second EC tube 16I connected between the second EC terminal 28*d* of the bioreactor 21 and the cassette 10.

A gas exchanger 29 that mixes a predetermined gas component with the liquid (e.g., the culture medium) is provided at an intermediate position of the first EC tube 16H. As an example of the gas component to be mixed, there may be cited a gas component that approximates the mixing ratio of natural air (nitrogen N2: 75%, oxygen O2: 20%, and carbon dioxide CO2: 5%).

The structure of the gas exchanger 29 is not particularly limited, and in the same manner as the bioreactor 21, a structure can be applied in which a plurality of hollow fibers 29*b* are provided inside a container 29*a*. More specifically, the gas exchanger 29 guides the liquid flowing through the first EC tube 16H into the inner cavities of the hollow fibers 29*b*, and during movement thereof inside the hollow fibers 29*b*, the gas component that is supplied to the interior of the container 29*a* (e.g., the space on the outer side of the hollow fibers 29*b*) is mixed with the liquid through the pores of the hollow fibers 29*b*.

By joining the aforementioned tubes 16 in advance, the cassette 10, which is one component of the kit 12, functions as a relay unit for the liquid pathways through which the cell solution, the cleaning solution, the culture solution, and the stripping solution of the respective medical bags 18 are allowed to flow to a different medical bag 18 or to the bioreactor 21. When the kit 12 is set in the cell propagation device 15, the cassette 10 is mounted in a cassette setting location inside the cell propagation device 15, which simplifies the wiring operation of the tubes 16 in the propagation process.

Figure 3:
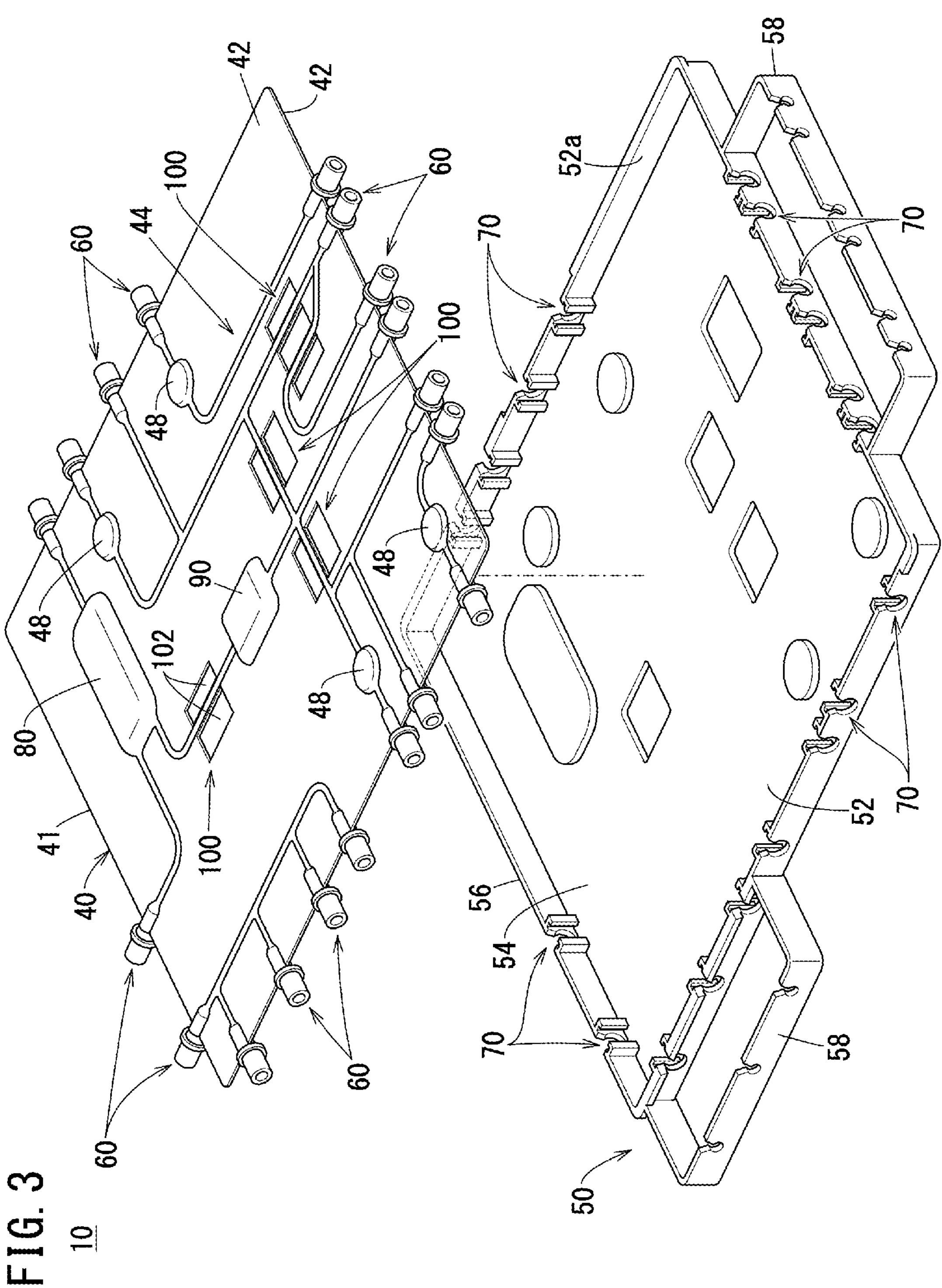
FIG. 3 is an exploded perspective view of the biological component cassette according to embodiments of the present disclosure.

As shown in FIG. 3, the cassette 10 is constituted by a soft cassette main body 40 to which the plurality of tubes 16 are directly connected, and a rigid frame 50 that retains the cassette main body 40 and is fixed to the cell propagation device 15.

The cassette main body 40 exhibits a substantially rectangular shape, and is formed in a thin sheet shape which possesses flexibility. The cassette main body 40 is formed by stacking and joining (e.g., fusion bonding) together two resin sheets 42 made of a resin material in a thickness direction. In the fusion bonding of the pair of resin sheets 42, gas is supplied to and discharged between the pair of resin sheets 42 along grooves that are formed in a fusion bonding mold, whereby flow path walls, in which the resin sheets 42 are raised and protrude with semicircular shapes in cross-section, and flow paths 44 are formed on the inner sides thereof. The material constituting the resin sheets 42 is not particularly limited, insofar as it possesses flexibility that is capable of being deformed by the pressure of the liquids, and for example, a vinyl chloride resin, a polyolefin resin, a polyurethane resin, or the like may be applied thereto. An embossing process may be implemented on the surface of the cassette main body 40, and fine convex/concave irregularities may be formed therein. A plurality of connectors 60 for connection between the plurality of tubes 16 and the flow paths 44 are provided on outer edges 41 of the cassette main body 40.

Further, in the cassette main body 40, a plurality of pressure target detection units 48, a liquid level target detection unit 80, and a check valve unit 90 are provided which communicate with the flow paths 44. Furthermore, the cassette main body 40 is equipped with flow path opening/closing units 100 (e.g., a plurality of cutouts 102) which are capable of opening and closing predetermined flow paths 44 at a plurality of locations.

On the other hand, the frame 50 is constituted by a resin material that is harder (having a greater modulus of elasticity) than the cassette main body 40, and is formed in a thin recessed shape having an accommodation space 52 therein in which the cassette main body 40 is accommodated. The constituent material of the frame 50 is not limited to any particular material, however, there may preferably be used a thermoplastic resin material, for example, polypropylene, polycarbonate, polyamide, polysulfone, polyarylate, methacrylate-butylene-styrene copolymer, or the like.

The frame 50 includes a substantially rectangular shaped cover member 54 which is slightly larger than the cassette main body 40, and side portions 56 that protrude a short distance from the outer periphery of the cover member 54 in a direction perpendicular to the cover member 54. The side portions 56 extend around the entire outer periphery of the cover member 54. In the frame 50, the accommodation space 52 is opened through an opening 52*a* surrounded by the side portions 56 on an opposite side from the cover member 54, thereby allowing one surface of the cassette main body 40 to be exposed. Further, the frame 50 includes a retaining frame 58 that extends outwardly from the upper side and the right side of the side portions 56, and retains the tubes 16 which are separated a predetermined distance from the side portions 56. Engaging portions 70 in which the respective connectors 60 are arranged and retained are provided in the side portions 56 at positions corresponding to each of the connectors 60 of the cassette main body 40.

The connectors 60 and the engaging portions 70 are disposed respectively on four sides of the substantially rectangular shaped cassette 10. Consequently, the frame 50 retains the sheet-shaped cassette main body 40 in a stretched state, and satisfactorily causes the flow paths 44 to be extended along a planar direction.

Figure 4:
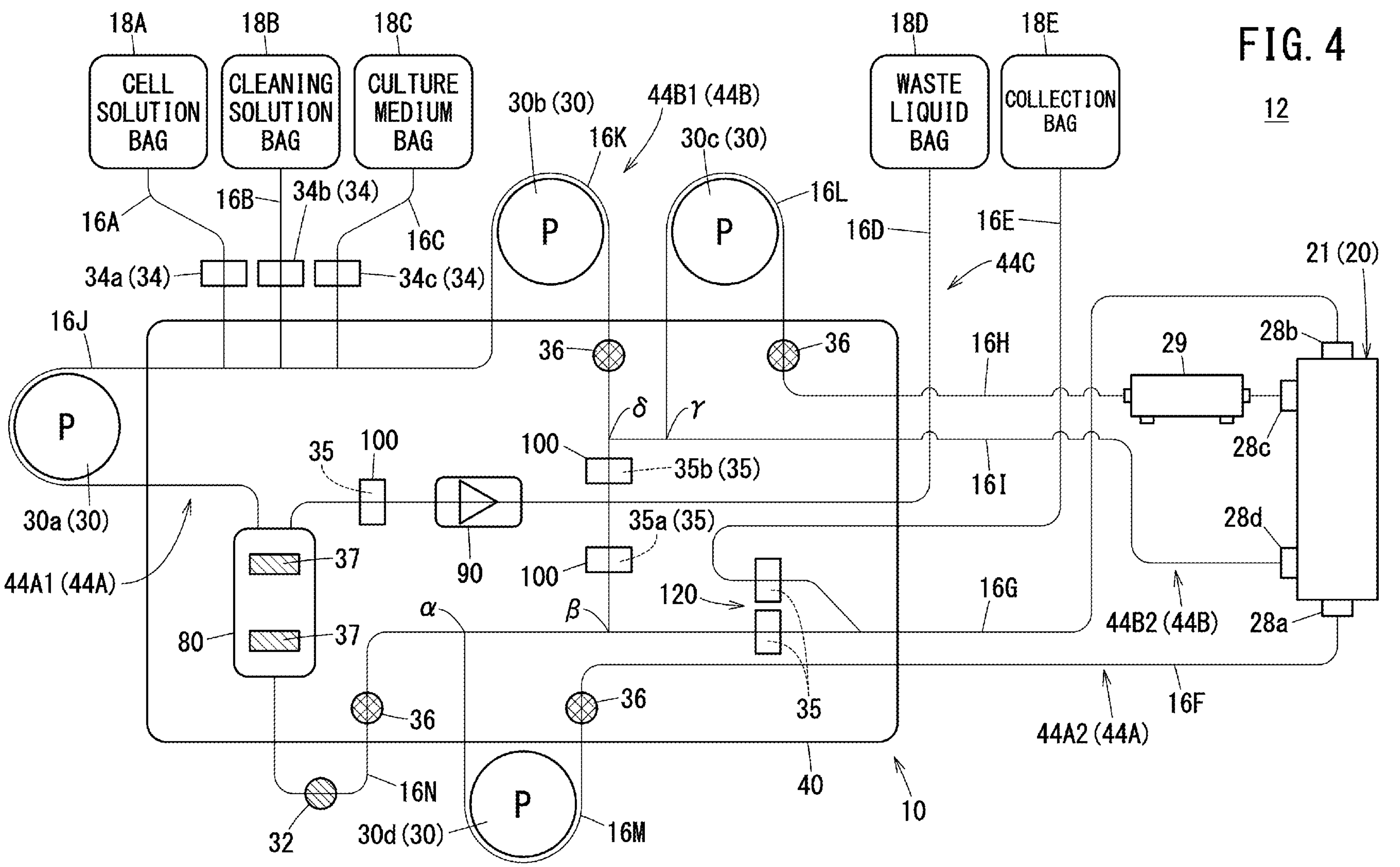
FIG. 4 is an explanatory diagram showing liquid pathways of the biological component kit according to embodiments of the present disclosure.

In the cell propagation system 23, in a state in which the kit 12 (including the cassette 10) is set in the cell propagation device 15, pathways for the liquids (the cell solution, the cleaning solution, the culture medium, etc.) are formed as shown in FIG. 4. Further, in the set state, four pumps 30 (first to fourth pumps 30*a* to 30*d*) are arranged at positions in close proximity to the sides of the cassette 10. By being rotated in a squeezing manner around the respective pump tubes 16J to 16M that project out from the cassette 10, the first to fourth pumps 30*a* to 30*d* apply a fluid force to the liquids inside the pump tubes 16J to 16M.

Further, in the cell propagation system 23, a sensor tube 16N is arranged to face toward an air bubble sensor 32 in the set state. Outer side clamps 34 that open and close internal flow paths are arranged on the cell solution tube 16A, the cleaning solution tube 16B, and the culture medium tube 16C. More specifically, a first outer side clamp 34*a* is arranged on the cell solution tube 16A, a second outer side clamp 34*b* is arranged on the cleaning solution tube 16B, and a third outer side clamp 34*c* is arranged on the culture medium tube 16C.

Further, inside the cassette 10, in the set state, pressure sensors 36 face toward the pressure target detection units 48, respectively, and liquid level sensors 37 face toward the liquid level target detection unit 80. Inner side clamps 35 are arranged respectively in each of the flow path opening/closing units 100 (the cutouts 102).

Figure 5:
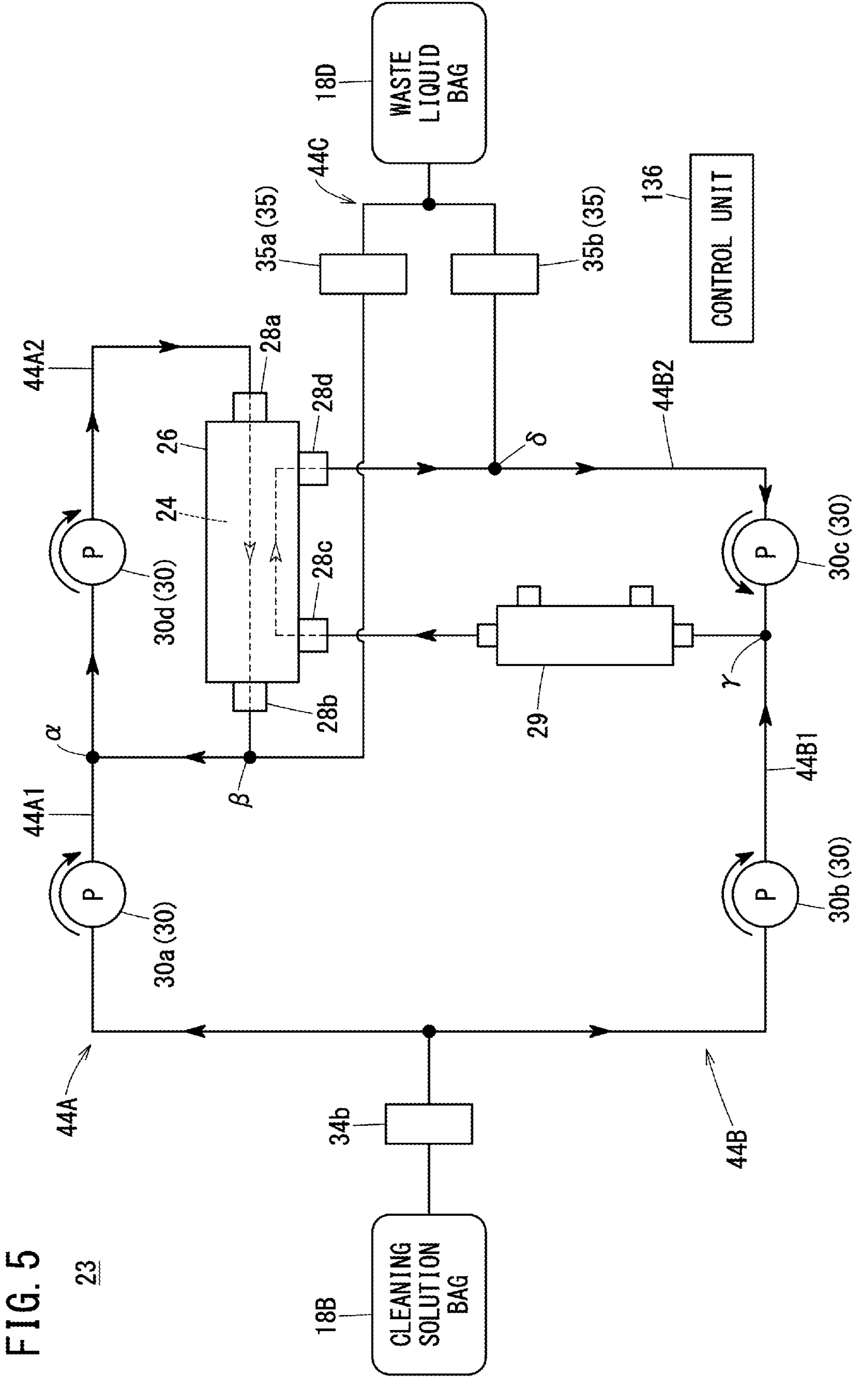
FIG. 5 is an explanatory diagram schematically showing the liquid pathways at a time of priming according to embodiments of the present disclosure.

Although a detailed description thereof is omitted, the flow paths 44 inside the cassette 10 (the cassette main body 40) are constituted by an IC route 44A (internal route) for supplying liquid to the inner cavities 24*a* of the hollow fibers 24 together with the first and second IC tubes 16F and 16G, and an EC route 44B (external route) for supplying liquid to the outer side (the main space 26*a*) of the hollow fibers 24 together with the first and second EC tubes 16H and 16I. In particular, at a time of priming of the bioreactor 21, the outer side clamps 34 and the inner side clamps 35 are appropriately opened or closed, whereby the IC route 44A and the EC route 44B of the kit 12 as a whole exhibit the state schematically illustrated in FIG. 5.

More specifically, the IC route 44A includes an IC supply circuit 44A1 through which the liquid can be supplied from the cleaning solution bag 18B to a predetermined position alpha downstream of the first pump 30*a* (refer also to FIG. 4), and an IC circulation circuit 44A2 in which the liquid can be circulated through the bioreactor 21 on a downstream side of the predetermined position alpha.

More specifically, the IC supply circuit 44A1 supplies the liquid (the cleaning solution) in the cleaning solution bag 18B to the IC circulation circuit 44A2 while being driven under operation of the first pump 30*a*. In addition to disposing the first pump 30*a*, the air bubble sensor 32, the pressure sensors 36, and the liquid level target detection unit 80, etc., are disposed along the IC supply circuit 44A1 (refer also to FIG. 4).

The IC circulation circuit 44A2 is provided with the fourth pump 30*d*, and is connected to the first IC terminal 28*a* and the second IC terminal 28*b* of the bioreactor 21. Accordingly, the liquid inside the IC circulation circuit 44A2 flows into the inner cavities 24*a* of the hollow fibers 24 under a driving action of the fourth pump 30*d*. Further, a waste liquid route 44C, which is connected to the waste liquid bag 18D, is connected to a predetermined position beta (refer also to FIG. 4) of the IC circulation circuit 44A2. Accordingly, the liquid that circulates in the IC circulation circuit 44A2 is discharged into the waste liquid bag 18D via the waste liquid route 44C, in a state in which an IC waste liquid clamp 35*a* (inner side clamp 35) provided in the waste liquid route 44C is opened.

On the other hand, the EC route 44B includes an EC supply circuit 44B1 which is capable of supplying the liquid from the cleaning solution bag 18B to a predetermined position gamma downstream of the second pump 30*b* (refer to FIG. 4), and an EC circulation circuit 44B2 which is capable of circulating the liquid through the bioreactor 21 on the downstream side of the predetermined position gamma.

The EC supply circuit 44B1 supplies the liquid (e.g., the cleaning solution) inside the cleaning solution bag 18B to the EC circulation circuit 44B2 while being driven under operation of the second pump 30*b*. On the other hand, in the EC circulation circuit 44B2, the third pump 30*c* is disposed, and further, is connected to the first EC terminal 28*c* and the second EC terminal 28*d* of the bioreactor 21. Accordingly, the liquid inside the EC circulation circuit 44B2 flows into the main space 26*a* of the container 26 under a driving action of the third pump 30*c*. Further, the waste liquid route 44C is connected to a predetermined position delta of the EC circulation circuit 44B2. Accordingly, the liquid that circulates in the EC circulation circuit 44B2 is discharged into the waste liquid bag 18D via the waste liquid route 44C, in a state in which an EC waste liquid clamp 35*b* (inner side clamp 35) provided in the waste liquid route 44C is opened.

It should be noted that the cell propagation system 23 is not particularly limited in terms of the liquids that are used during priming (in other words, the medical bags 18 connected to the IC supply circuit 44A1 and the EC supply circuit 44B1). For example, the cell propagation system 23 may be constituted to be connected to the culture medium bag 18C, and make use of the culture medium as the priming liquid.

Returning to FIG. 1, the cell propagation device 15 in which the kit 12 is mounted is equipped with a box-shaped device main body 130, and a stand 132 on which the respective medical bags 18 of the kit 12 are retained. Further, a touch panel 134 (e.g., a display operation unit) for carrying out operations and displays when the propagation process is performed, is provided on an outer surface of the device main body 130. Furthermore, in the interior of the device main body 130, there are provided a cassette placement unit (not shown) in which the cassette 10 is fixed in an upright posture, and further, the bioreactor 21 is retained at an appropriate height, and a control unit 136 that controls operation of the cell propagation system 23.

The control unit 136 is constituted in a computer having a processor, a memory, and an input/output interface, none of which are illustrated. By the control unit 136 executing a program (not shown) stored in the memory, the control unit 136 causes the pumps 30, the outer side clamps 34, the inner side clamps 35, and the like to be appropriately operated in a cell propagation process. In particular, during priming inside the kit 12, the control unit 136 executes the process flow described below, thereby sufficiently discharging the air from the interior of the membrane structure 25 (the pores 25*a*) of the hollow fibers 24.

The cell propagation system 23 according to the present embodiment is basically constituted in the manner described above. Next, a description will be given below concerning the priming method and operations of the propagation process.

As shown in FIG. 1, in the propagation process of the cell propagation system 23, an operator inserts portions of the kit 12 including the cassette 10 into the cell propagation device 15, and together therewith, suspends the respective medical bags 18 of the kit 12 on the stand 132. Further, the operator places the appropriate tubes 16 of the kit 12 on the pumps 30, the air bubble sensor 32, and the outer side clamps 34 of the cell propagation device 15. Furthermore, in setting the cassette 10, the flow path opening/closing units 100 are arranged on the inner side clamps 35, the pressure target detection units 48 are arranged on the pressure sensors 36, and the liquid level target detection unit 80 is arranged on the liquid level sensors 37. Consequently, the pathways shown in FIG. 4 are constructed in the cell propagation system 23.

Figure 6B:
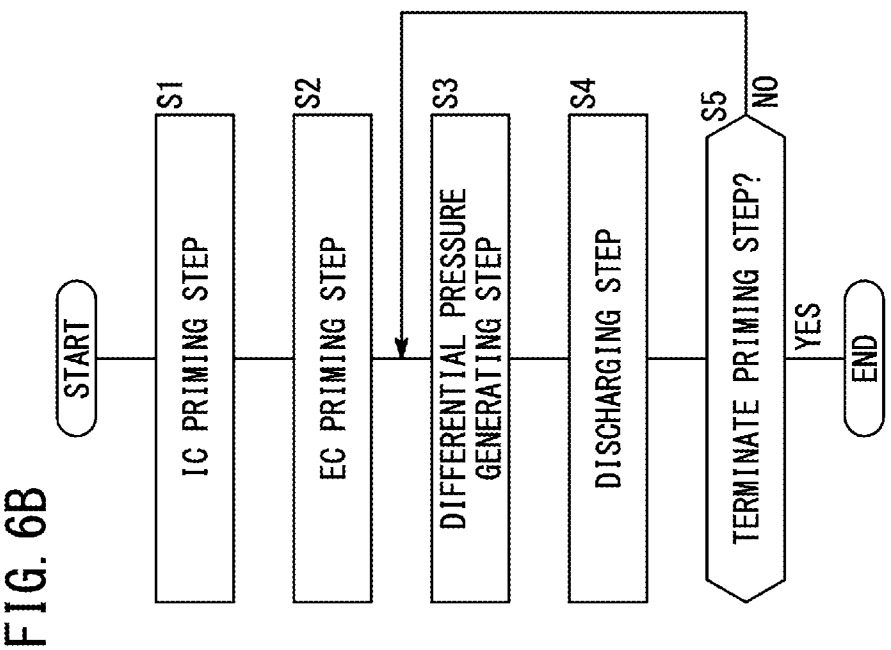
FIG. 6B is a flowchart showing a process flow of a priming step according to embodiments of the present disclosure.
Figure 6A:
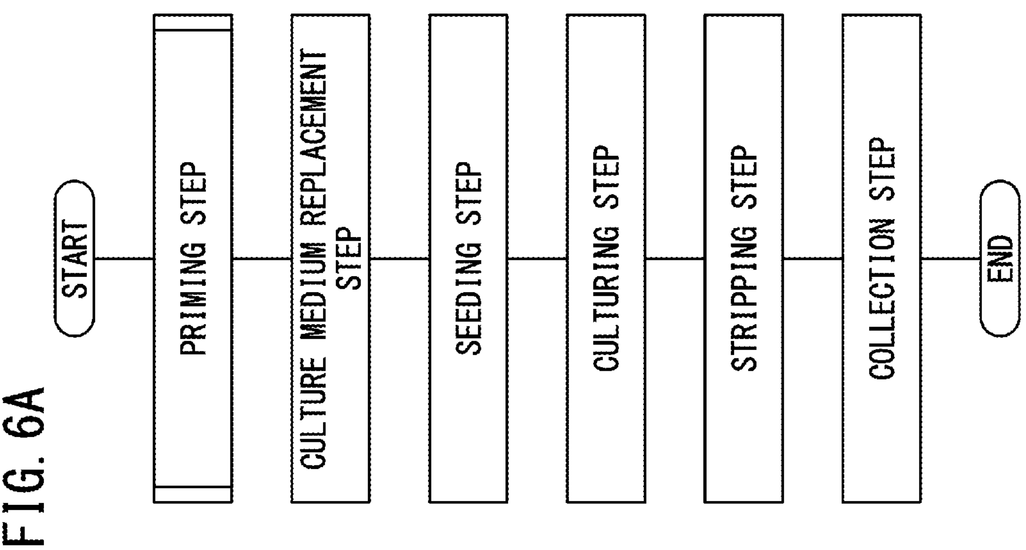
FIG. 6A is a flowchart showing a process flow of the biological component treatment system according to embodiments of the present disclosure.

After having been set, in the propagation process, as shown in FIG. 6A, a priming step, a culture medium replacement step, a seeding step, a culturing step, a stripping step, and a collection step are sequentially performed. Further, in the priming step, the process flow (e.g., the priming method) shown in FIG. 6B is carried out in order to sufficiently remove the air inside the kit 12 including the bioreactor 21.

Figure 7:
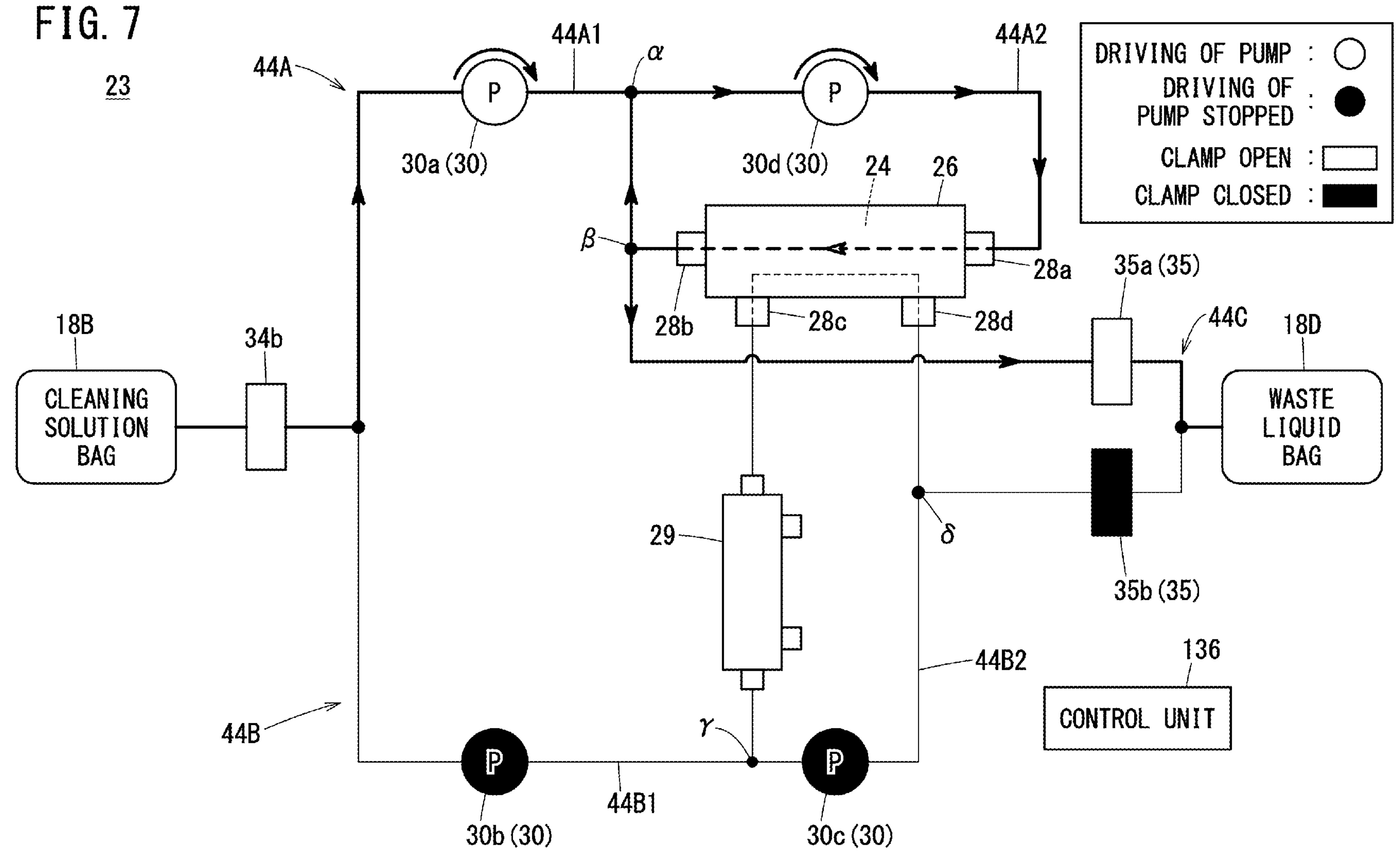
FIG. 7 is a schematic diagram showing operations of an IC priming step according to embodiments of the present disclosure.

In the priming step, the cell propagation system 23 initially performs an operation of allowing the cleaning solution to flow through the IC route 44A (step S1: IC priming step). More specifically, as shown in FIG. 7, the control unit 136 opens the second outer side clamp 34*b* together with rotating the first pump 30*a* and the fourth pump 30*d* at an appropriate speed, while on the other hand, the second pump 30*b* and the third pump 30*c* are placed in a state in which driving thereof is stopped. Consequently, the cleaning solution in the cleaning solution bag 18B is supplied to the bioreactor 21 via the IC route 44A (e.g., the IC supply circuit 44A1 and the IC circulation circuit 44A2). Inside the bioreactor 21, the cleaning solution flowing through the IC route 44A flows into the inner cavities 24*a* of the hollow fibers 24 and the air inside the hollow fibers 24 is removed, and the air is discharged to the exterior of the bioreactor 21 (e.g., the IC circulation circuit 44A2). At this time, in the cell propagation system 23, the IC air may be removed by rotating the bioreactor 21 in a vertical direction, disposing the second IC terminal 28*b* at a lower end, and disposing the first IC terminal 28*a* at an upper end.

Further, in the IC priming step, the control unit 136 opens the IC waste liquid clamp 35*a* of the waste liquid route 44C. Consequently, the air existing in the IC route 44A is discharged together with the cleaning solution from the IC circulation circuit 44A2 into the waste liquid bag 18D via the waste liquid route 44C.

Figure 8:
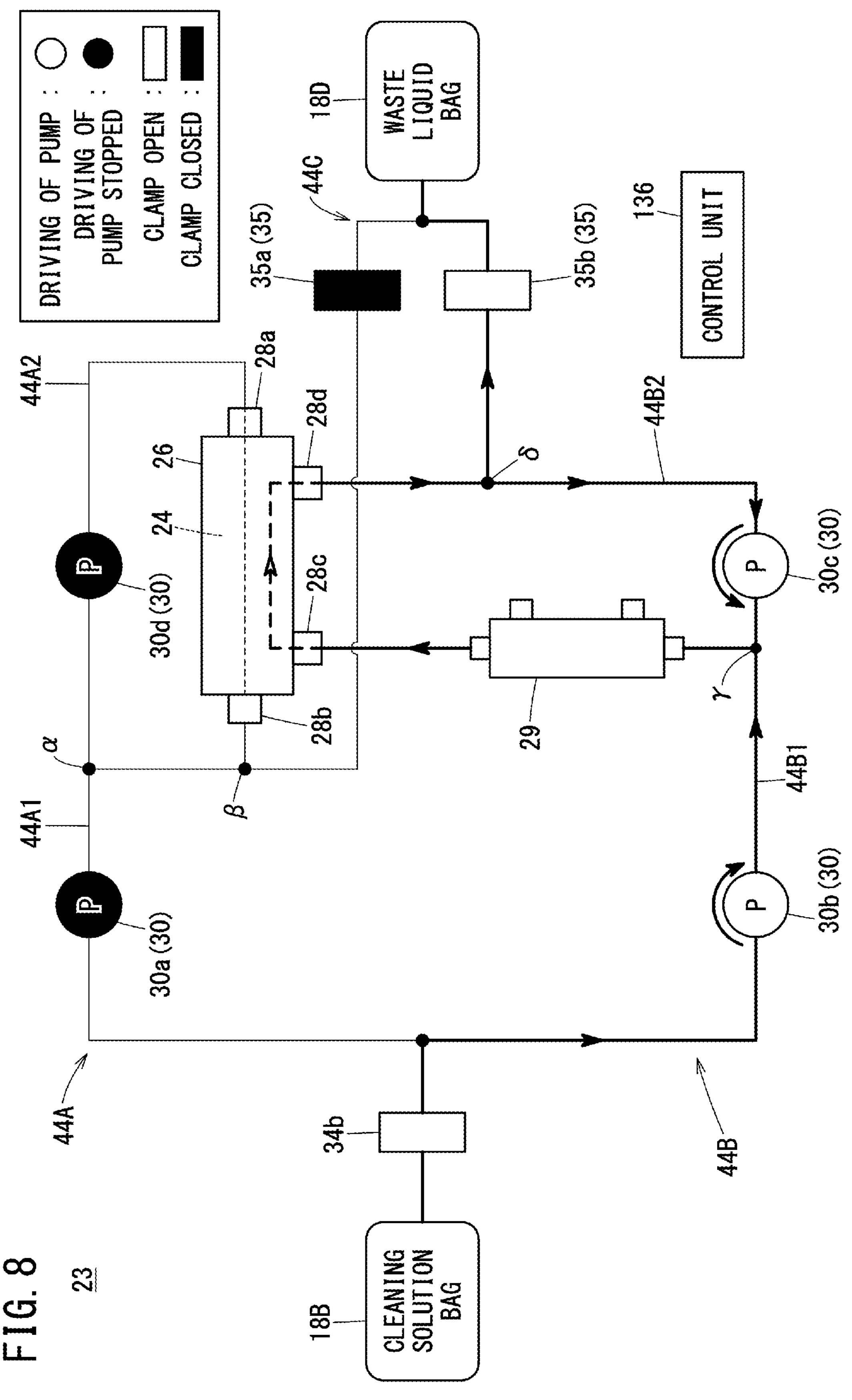
FIG. 8 is a schematic diagram showing operations of an EC priming step according to embodiments of the present disclosure.

Next, the cell propagation system 23 performs an operation of allowing the cleaning solution to flow through the EC route 44B (step S2: EC priming step). More specifically, as shown in FIG. 8, while the open state of the second outer side clamp 34*b* is maintained, the control unit 136 rotates the second pump 30*b* and the third pump 30*c* at an appropriate speed, while on the other hand, the first pump 30*a* and the fourth pump 30*d* are placed in a state in which driving thereof is stopped. Consequently, the cleaning solution in the cleaning solution bag 18B is supplied to the bioreactor 21 via the EC route 44B (the EC supply circuit 44B1 and the EC circulation circuit 44B2). Inside the bioreactor 21, the cleaning solution flowing through the EC route 44B flows into the main space 26*a* of the container 26 thereby removing the air, and the air is discharged to the exterior of the bioreactor 21 (e.g., the EC circulation circuit 44B2). At this time, the cell propagation system 23 may cause the bioreactor 21 to be rotated in the horizontal direction to thereby remove the EC air. In the cell propagation system 23, by causing the bioreactor 21 to be rotated in the vertical direction and the horizontal direction, removal of the air may be promoted.

Further, in the EC priming step, the control unit 136 opens the EC waste liquid clamp 35*b* of the waste liquid route 44C. Consequently, the air existing in the EC route 44B is discharged together with the cleaning solution from the EC circulation circuit 44B2 into the waste liquid bag 18D via the waste liquid route 44C.

Figure 9:
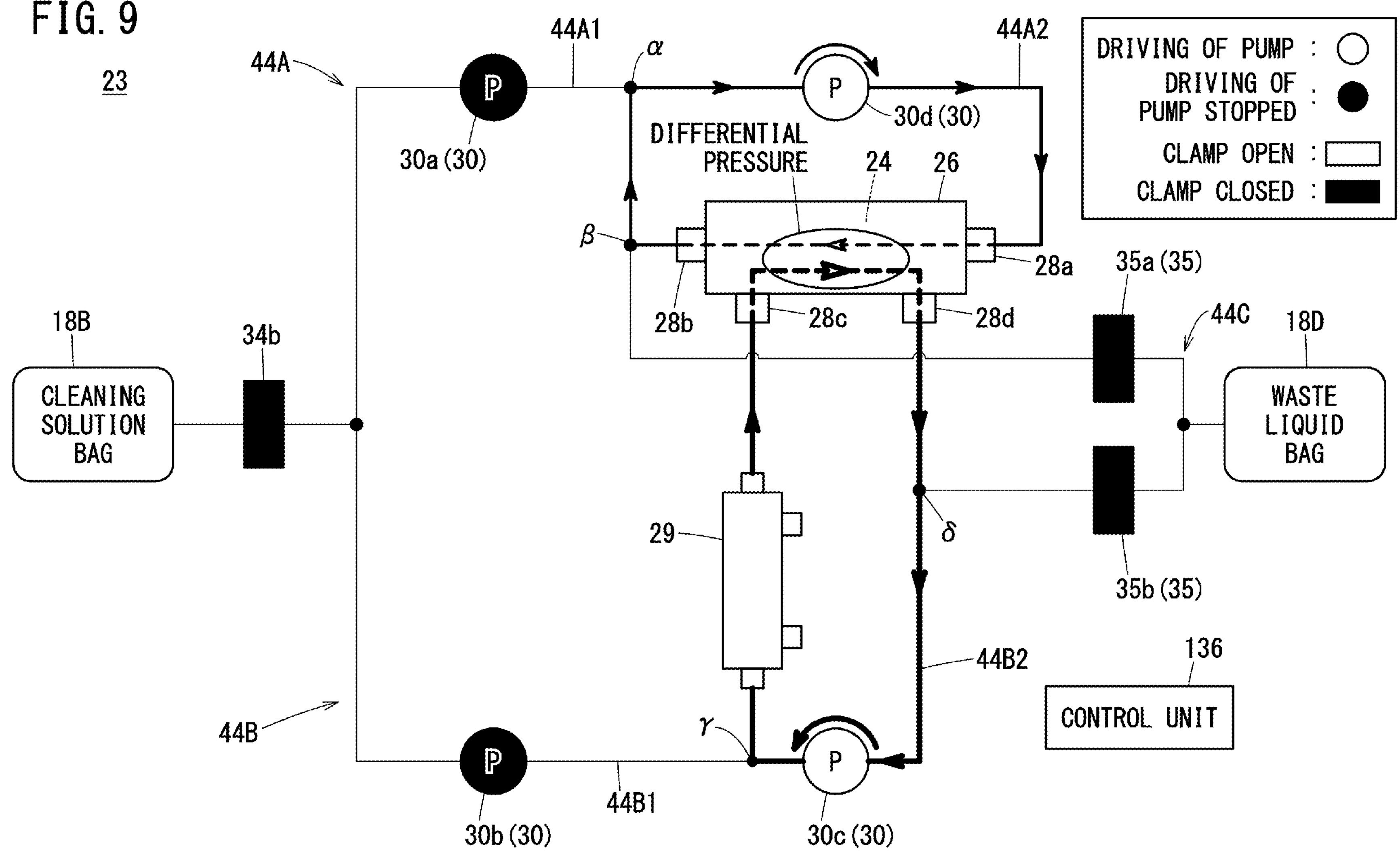
FIG. 9 is a schematic diagram showing operations of a differential pressure generating step according to embodiments of the present disclosure.

Furthermore, the cell propagation system 23 performs an operation of circulating the cleaning solution in both the IC route 44A and the EC route 44B, and at this time, a differential pressure is generated between both of such routes (step S3: differential pressure generating step). At this time, as shown in FIG. 9, the control unit 136 places the first pump 30*a* and the second pump 30*b* in a state in which driving thereof is stopped, while on the other hand, causes the fourth pump 30*d* of the IC circulation circuit 44A2, and the third pump 30*c* of the EC circulation circuit 44B2 to be rotated.

In addition, the control unit 136 carries out a control in which the flow rate of the cleaning solution in the EC circulation circuit 44B2 by the third pump 30*c* is made more rapid than the flow rate of the cleaning solution in the IC circulation circuit 44A2 by the fourth pump 30*d*. For example, the control unit 136 sets the flow rate of the cleaning solution in the IC circulation circuit 44A2 to 25 ml/min, and sets the flow rate of the cleaning solution in the EC circulation circuit 44B2 to 250 ml/min. Due to the difference in speed between the cleaning solution flowing in the IC circulation circuit 44A2 and the cleaning solution flowing in the EC circulation circuit 44B2, a differential pressure of the cleaning solution is generated in the hollow fibers 24 where the IC circulation circuit 44A2 and the EC circulation circuit 44B2 are in contact (where a boundary is formed therebetween).

In this instance, as shown in FIG. 2, in each of the hollow fibers 24, by the coating 27 being formed on the inner circumferential surface of the membrane structure 25, it becomes difficult for the air inside the (pores 25*a* of the) membrane structure 25 to escape. However, in the cell propagation system 23 according to the present embodiment, by the pressure in the inner cavities 24*a* being made lower with respect to the pressure in the main space 26*a* on the outer side of the hollow fibers 24 (e.g., due to the differential pressure being generated), the cleaning solution easily permeates into the pores 25*a*.

Accordingly, due to the differential pressure, a force acts on the air inside the membrane structure 25 such that the air is moved toward the side of the inner cavities 24*a*. In particular, the differential pressure due to the difference between the flow rate of the cleaning solution in the IC circulation circuit 44A2 and the flow rate of the cleaning solution in the EC circulation circuit 44B2 does not impart a motive force to the cleaning solution or the air sufficient enough for the coating 27 to be peeled off from the membrane structure 25, and therefore, the coating 27 can be suitably maintained.

The ratio (e.g., the speed ratio) of the flow rate of the EC circulation circuit 44B2 with respect to the flow rate of the IC circulation circuit 44A2, although not particularly limited, is set, for example, on the order of 5 times faster to 15 times faster. In the case that the speed ratio is less than 5 times, the differential pressure between the IC circulation circuit 44A2 and the EC circulation circuit 44B2 is small, and time is required for the action of the air from the EC circulation circuit 44B2 to be moved to the IC circulation circuit 44A2. On the other hand, in the case that the speed ratio is greater than or equal to 15 times, the differential pressure between the IC circulation circuit 44A2 and the EC circulation circuit 44B2 becomes excessive, and it is possible for the coating 27 inside the membrane structure 25 to be peeled off when the air moves from the EC circulation circuit 44B2 to the IC circulation circuit 44A2.

Thereafter, the cell propagation system 23 carries out an operation of discharging from the IC circulation circuit 44A2, together with the cleaning solution, the air that is discharged into the IC route 44A in accordance with execution of step S3 (step S4: discharging step). In step S4, similar to step S1 (refer to also FIG. 7), the control unit 136 opens the second outer side clamp 34*b* together with rotating the first pump 30*a* and the fourth pump 30*d* at an appropriate speed, while on the other hand, the second pump 30*b* and the third pump 30*c* are placed in a state in which driving thereof is stopped. Further, the control unit 136, by opening the IC waste liquid clamp 35*a*, opens into operation the waste liquid route 44C from the IC circulation circuit 44A2. At this time, in the cell propagation system 23, the IC air may be removed by rotating the bioreactor 21 in a vertical direction, disposing the second IC terminal 28*b* at a lower end, and disposing the first IC terminal 28*a* at an upper end.

Consequently, in the IC circulation circuit 44A2, while the cleaning solution is supplied from the cleaning solution bag 18B (e.g., the IC supply circuit 44A1), the air and the cleaning solution, which are discharged from the membrane structure 25 of the hollow fibers 24, can be guided to the waste liquid route 44C. In addition, the cleaning solution and the air that have flowed through the waste liquid route 44C are smoothly discharged into the waste liquid bag 18D.

After completion of step S4, the cell propagation system 23 determines whether or not to terminate the priming step (step S5: determination step). In the determination step, for example, the control unit 136 counts the execution time period of the priming step, or the number of times that step S3 and step S4 are executed. Then, if the content of the count is less than or equal to a predetermined threshold value (step S5: NO), the control unit 136 returns to step S3 and the subsequent process flow is repeated. On the other hand, if the content of the count exceeds the predetermined threshold value (step S5: YES), a determination is made that the air has escaped from the bioreactor 21, and the priming process is brought to an end.

Returning to FIG. 6A, the cell propagation system 23 carries out the culture medium replacement step after completion of the priming step, and guides the culture medium in the culture medium bag 18C to the predetermined tubes 16, the bioreactor 21, and the flow paths 44 of the cassette main body 40, etc., which are filled with the culture medium. In addition, the cell propagation system 23 carries out the seeding step after completion of the medium replacement step. At this time, in the cell propagation system 23, while the cell solution of the cell solution bag 18A is supplied via the IC route 44A to (e.g., the inner cavities 24*a* of) the hollow fibers 24 of the bioreactor 21, the culture medium existing in the EC route 44B is circulated, and the gas component is supplied to the bioreactor 21. In the seeding step, since the coating 27 on the interior of the hollow fibers 24 is suitably maintained, the cells can be made to smoothly adhere with respect to the coating 27.

Furthermore, after completion of the seeding step, the cell propagation system 23 performs the culturing step of culturing the cells. In the culturing step, the culture medium is supplied from both the IC route 44A and the EC route 44B, and cultures the cells inside the hollow fibers 24. The culturing step is carried out for a longer period of time (for example, over several days) in comparison with the other steps, whereby the cells are made to propagate on the coating 27. Moreover, in the cell propagation system 23, an operation of supplying the culture medium from the EC route 44B without using the IC route 44A may be carried out in the culturing step.

Further, in the stripping step after having performed the culturing step, the stripping solution is supplied from the IC route 44A to thereby strip off the cells that were cultured (e.g., propagated) inside the bioreactor 21. In the collection step after having performed the stripping step, by supplying the culture medium to the IC route 44A, the cells that were stripped off in the stripping step are made to flow out from the bioreactor 21, and are guided into the collection bag 18E. At this time, the culture medium and the gas component are also supplied through the EC route 44B.

By the aforementioned steps, in the cell propagation system 23, the cells that were cultured in the bioreactor 21 can be satisfactorily stored in the collection bag 18E. In particular, in the cell propagation system 23, in the priming step, it is possible to sufficiently remove the air from the membrane structure 25 of the hollow fibers 24, and a failure in propagation of the cells due to remaining air can be avoided.

The present disclosure is not limited to the above-described embodiment, and various modifications can be adopted in accordance with the essence and gist of the present disclosure. For example, in the cell propagation system 23, constitution may be provided in which, without performing the IC priming step or the EC priming step, the cleaning solution is simultaneously supplied to the IC circulation circuit 44A2 and the EC circulation circuit 44B2, and a differential pressure is generated between the IC circulation circuit 44A2 and the EC circulation circuit 44B2.

Further, the above-described biological component treatment system 22 (the cell propagation system 23) has been described as constitution in which the flexible cassette main body 40 (e.g., the cassette 10) is provided in the kit 12. However, constitution may be provided in which the kit 12 is not equipped with such a cassette 10, and a rigid cassette 10 may be applied thereto.

The priming method and the biological component treatment system 22 according to the present disclosure are not limited to the cell propagation system 23 that performs the cell propagation process, and can be applied to various systems in which priming with respect to the hollow fibers 24 is carried out. For example, the priming method and the biological component treatment system 22 of the present disclosure may be applied to a blood treatment system in which a blood treatment (e.g., such as filtration) is carried out.

Figure 10:
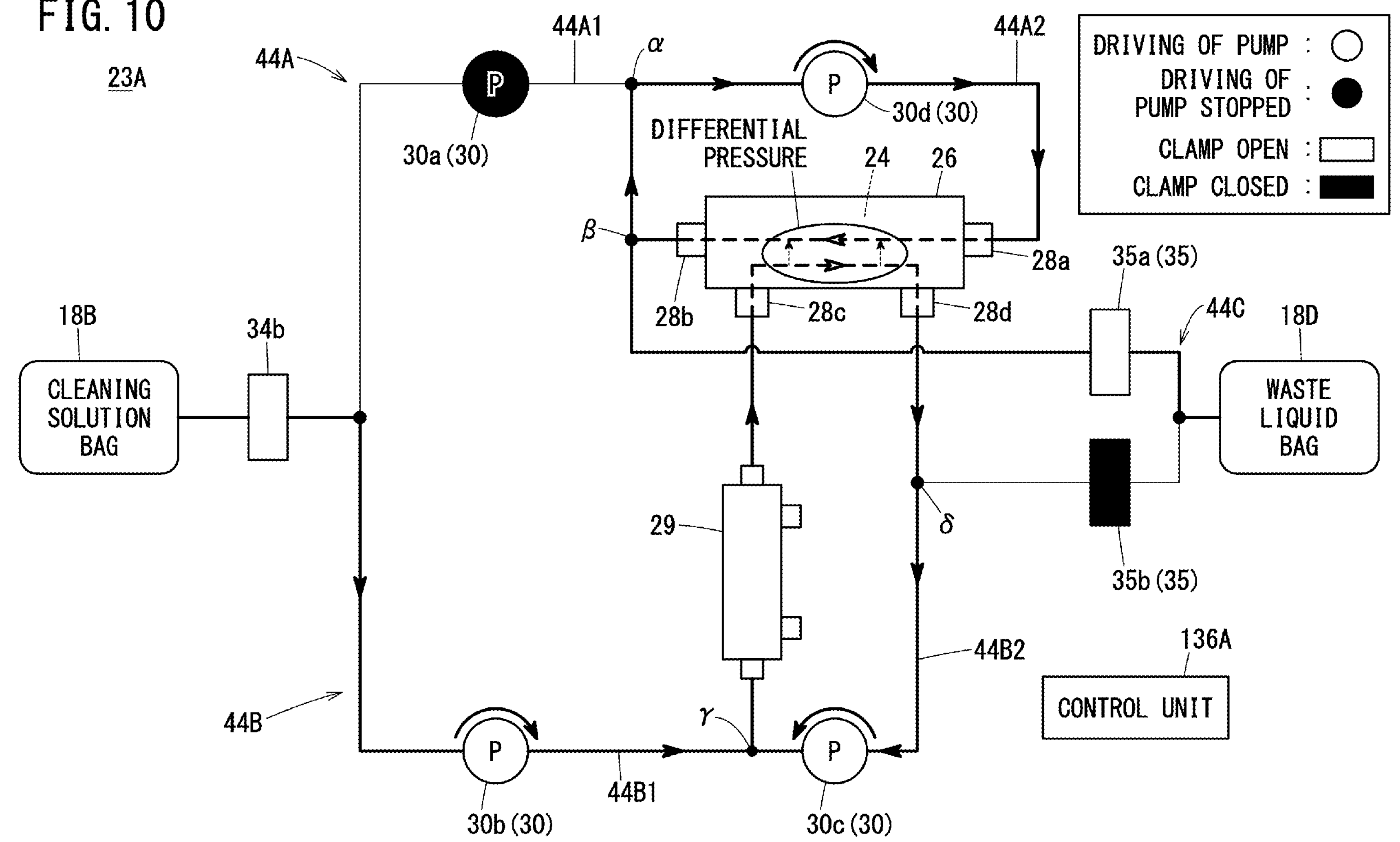
FIG. 10 is a schematic diagram showing the differential pressure generating step of the cell propagation system according to embodiments of the present disclosure.

As shown in FIG. 10, a cell propagation system 23A according to a second embodiment differs from the above-described cell propagation system 23, in that a liquid (the cleaning solution) is continuously supplied from the EC supply circuit 44B1 in order to generate a differential pressure between the IC route 44A and the EC route 44B. Moreover, the constitution by which the liquid is operated on in the cell propagation system 23A is the same as that of the cell propagation system 23, and only the control performed by a control unit 136A is different. Thus, a description will be given below concerning the priming method of the second embodiment.

The cell propagation system 23A executes the IC priming step and the EC priming step in the same manner as in the first embodiment, and thereafter, executes the differential pressure generating step which operates differently than in the first embodiment. In the differential pressure generating step, the control unit 136A opens the second outer side clamp 34*b* and the IC waste liquid clamp 35*a*, while on the other hand, closes the EC waste liquid clamp 35*b*. Further, while placing the first pump 30*a* in a state in which driving thereof is stopped, the control unit 136A causes the fourth pump 30*d* of the IC circulation circuit 44A2, the second pump 30*b* of the EC supply circuit 44B1, and the third pump 30*c* of the EC circulation circuit 44B2 to be rotated.

Consequently, while the cleaning solution is circulated by the third pump 30*c*, the EC circulation circuit 44B2 is supplied with the cleaning solution from the EC supply circuit 44B1. Therefore, the internal pressure inside the EC circulation circuit 44B2 becomes higher than the internal pressure inside the IC circulation circuit 44A2. Accordingly, in the cell propagation system 23A, in the hollow fibers 24 with which the IC circulation circuit 44A2 and the EC circulation circuit 44B2 are in contact, a state is brought about in which the pressure of the cleaning solution in the inner cavities 24*a* becomes lower (a differential pressure is generated) than the pressure of the cleaning solution in the main space 26*a*. As a result, a situation is brought about in which the cleaning solution in the main space 26*a* moves through the pores 25*a* to the side of the inner cavities 24*a* (the movement of the liquid is shown by the dashed lines in FIG. 10), and at this time, the air inside the membrane structure 25 can be discharged into the inner cavities 24*a*. At this time, in the cell propagation system 23A, the IC air may be removed by rotating the bioreactor 21 in a vertical direction, disposing the second IC terminal 28*b* at a lower end, and disposing the first IC terminal 28*a* at an upper end.

In the IC circulation circuit 44A2, the IC waste liquid clamp 35*a* is opened and the cleaning solution is circulated by the fourth pump 30*d*, whereby the cleaning solution can be smoothly discharged into the waste liquid route 44C (e.g., the waste liquid bag 18D) in accordance with the amount of movement of the cleaning solution from the EC circulation circuit 44B2.

Moreover, the control unit 136A of the cell propagation system 23A may carry out a control in which, in addition to supplying the cleaning solution from the EC supply circuit 44B1, the flow rate of the cleaning solution in the EC circulation circuit 44B2 is made more rapid than the flow rate of the cleaning solution in the IC circulation circuit 44A2. Alternatively, constitution may be provided in which, in the case that the cleaning solution is supplied from the EC supply circuit 44B1, the differential pressure of the cleaning solution is adjusted by making the flow rate of the cleaning solution in the EC circulation circuit 44B2 slower than the flow rate of the cleaning solution in the IC circulation circuit 44A2 (or alternatively, making the flow rates the same).

Further, in the cell propagation system 23A according to the second embodiment, even in the differential pressure generating step, the IC circulation circuit 44A2 and the waste liquid route 44C are connected, and the cleaning solution in which air is contained is discharged. Therefore, in the priming method, constitution may be provided in which the discharging step is not executed (e.g., the differential pressure generating step and the discharging step are not repeated).

Figure 11:
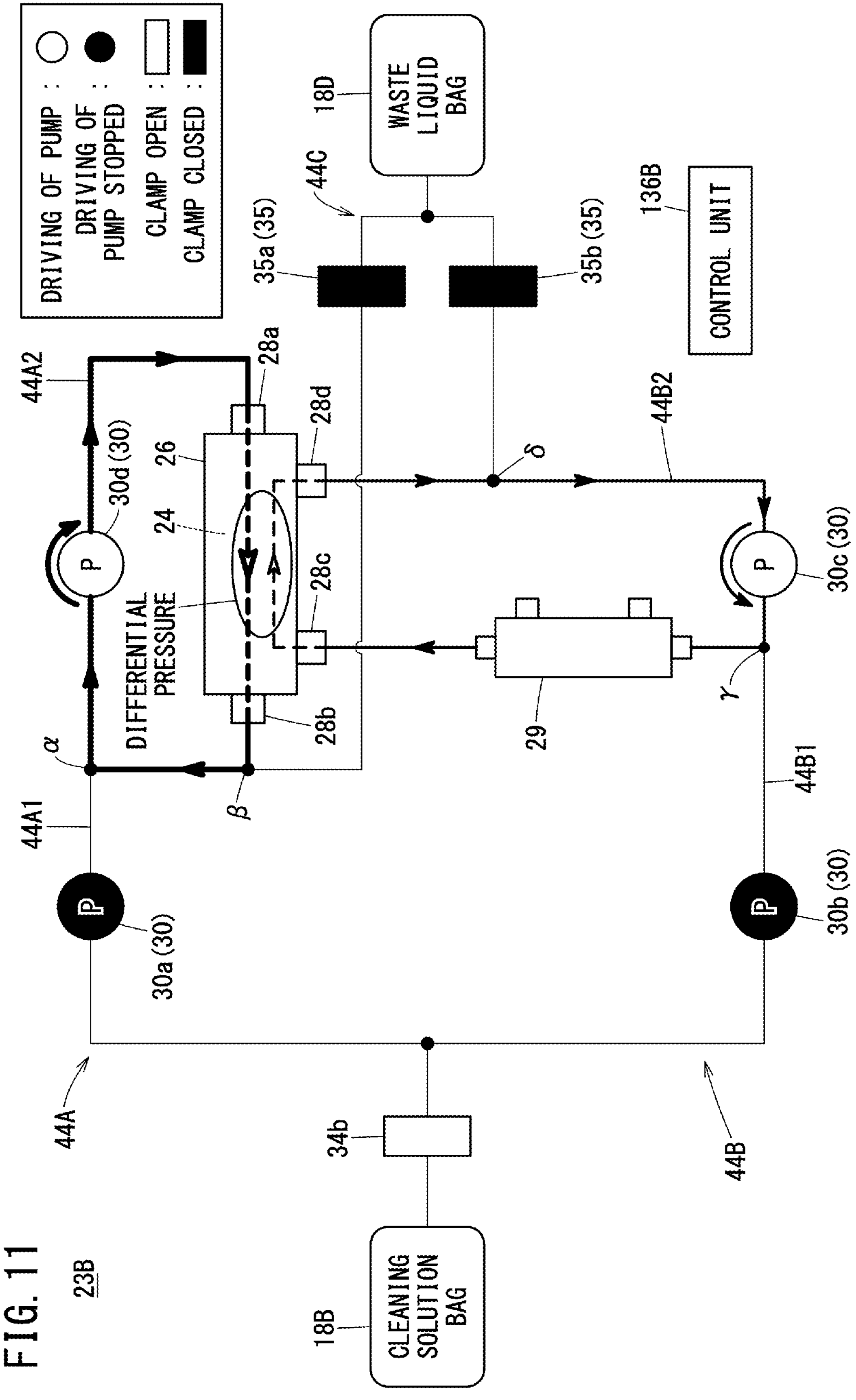
FIG. 11 is a schematic diagram showing the differential pressure generating step of the cell propagation system according to embodiments of the present disclosure.

As shown in FIG. 11, the cell propagation system 23B according to a third embodiment differs from the cell propagation systems 23 and 23A according to the first and second embodiments, in that a differential pressure is generated in a manner so that the internal pressure of the EC circulation circuit 44B2 becomes lower than the internal pressure of the IC circulation circuit 44A2. More specifically, after the IC priming step and the EC priming step have been executed in the same manner as in the first embodiment, a control unit 136B of the cell propagation system 23B places the first pump 30*a* and the second pump 30*b* in a state in which driving thereof is stopped, and a control is performed to make the flow rate of the cleaning solution in the IC circulation circuit 44A2 by the fourth pump 30*d* more rapid than the flow rate of the cleaning solution in the EC circulation circuit 44B2 by the third pump 30*c*. The ratio (speed ratio) of the flow rate of the IC circulation circuit 44A2 with respect to the flow rate of the EC circulation circuit 44B2, although not particularly limited, is set, for example, on the order of 5 times to 15 times.

Consequently, due to the difference in speed between the IC circulation circuit 44A2 and the EC circulation circuit 44B2, a differential pressure is generated in which, in the hollow fibers 24, the pressure of the IC circulation circuit 44A2 is higher than the pressure of the EC circulation circuit 44B2. Due to such a differential pressure, the air inside the membrane structure 25 moves to the side of the main space 26*a*. In particular, by the pressure of the IC circulation circuit 44A2 being made higher than the pressure of the EC circulation circuit 44B2, peeling of the coating 27 from the inner circumferential surfaces of the inner cavities 24*a* due to movement of the cleaning solution is suppressed, and the coating 27 can be satisfactorily maintained.

Figure 12:
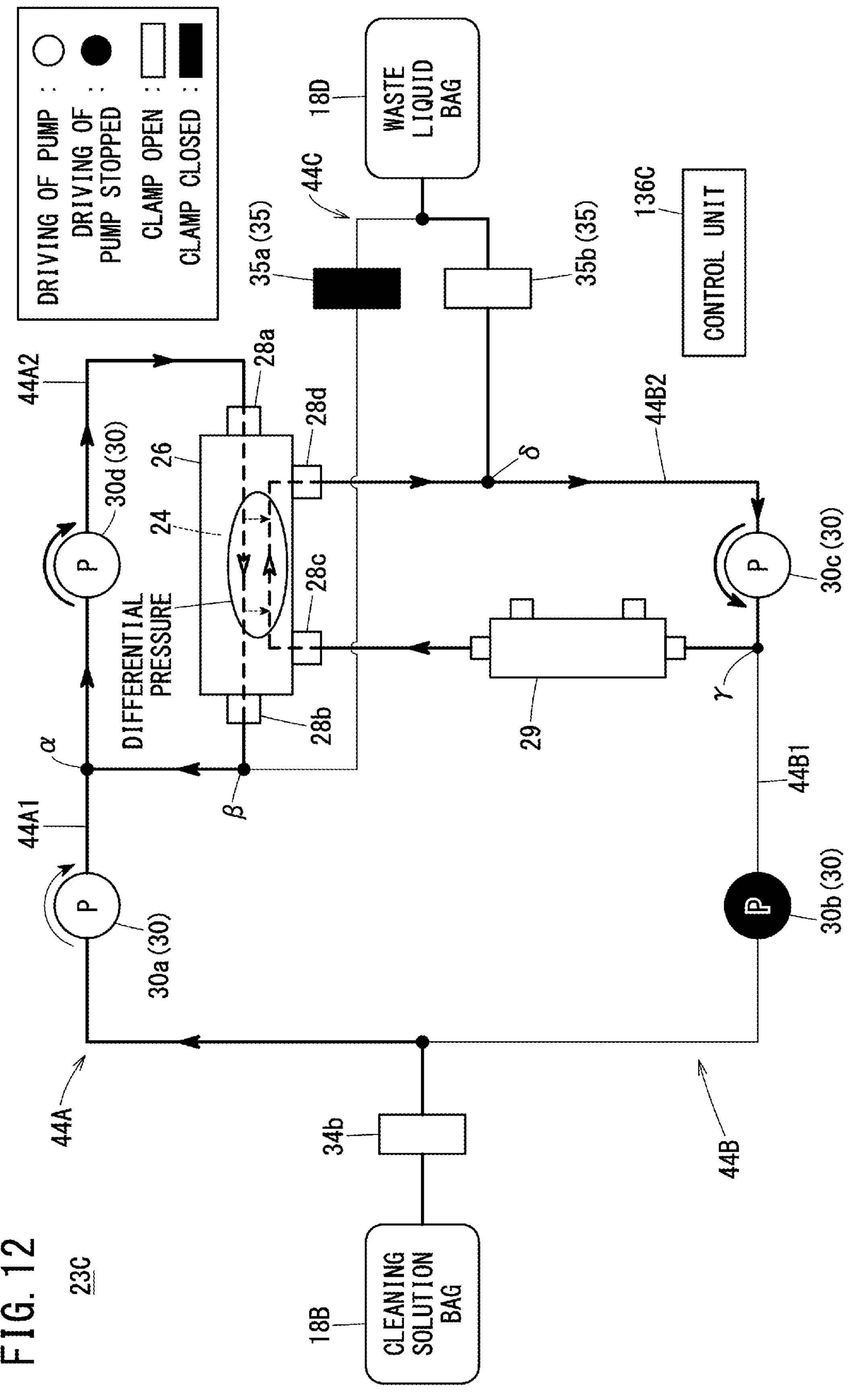
FIG. 12 is a schematic diagram showing the differential pressure generating step of the cell propagation system according to embodiments of the present disclosure.

As shown in FIG. 12, a cell propagation system 23C (control unit 136C) according to a fourth embodiment differs from the above-described cell propagation systems 23, 23A, and 23B, in that the cleaning solution is continuously supplied from the IC supply circuit 44A1 in order to generate the differential pressure. With such constitution in which the cleaning solution is continuously supplied from the IC supply circuit 44A1, the internal pressure in the IC circulation circuit 44A2 can be easily increased with respect to the internal pressure in the EC circulation circuit 44B2. As a result, a situation is brought about in which the cleaning solution in the inner cavities 24*a* moves through the pores 25*a* to the side of the main space 26*a* (the movement of the liquid is shown by the dashed lines in FIG. 12), and at this time, the air inside the membrane structure 25 can be discharged into the main space 26*a*. Thus, in the cell propagation system 23C as well, it is possible to rapidly discharge the air in the treatment unit 20 (the membrane structure 25 of the hollow fibers 24) via the EC route 44B.

It is a matter of course that, according to the present disclosure, portions or all of the priming methods of the cell propagation systems 23 and 23A to 23C described in each of the aforementioned embodiments can be taken and incorporated into other embodiments.

Technical concepts and effects that can be grasped from the above-described embodiments will be described below.

The first aspect of the present disclosure is characterized by the priming method for discharging the gas contained within the hollow fibers 24 by introducing a liquid into the treatment unit 20 including the hollow fibers 24 on which the coating 27 is formed on the inner circumferential surfaces that constitute the inner cavities 24*a* thereof, and the container 26 having the internal space (the main space 26*a*) in which the hollow fibers 24 are accommodated, wherein, in the treatment unit 20, there are connected the internal route (the IC route 44A) through which the liquid is allowed to flow in the inner cavities 24*a*, and the external route (the EC route 44B) through which the liquid is allowed to flow in the internal space on the outer side of the hollow fibers 24, and wherein, at the time of priming, while the liquid flows through both the internal route and the external route, a differential pressure is generated between the liquid flowing through the inner cavities 24*a* and the liquid flowing through the internal space, and the gas is made to flow out from the hollow fibers 24.

In the priming method described above, in the hollow fibers 24, by generating the differential pressure between the liquid flowing from the internal route (e.g., the IC route 44A) to the inner cavities 24*a*, and the liquid flowing from the external route (e.g., the EC route 44B) to the internal space (e.g., the main space 26*a*), the gas can be easily and reliably discharged from the hollow fibers 24. In particular, even with constitution in which the coating 27 is formed on the inner circumferential surfaces of the hollow fibers 24, the liquid is made to permeate into the membrane structure 25 based on the differential pressure between the inner cavities 24*a* of the hollow fibers 24 and the internal space, and it is possible to satisfactorily discharge the gas from the hollow fibers 24.

Further, the internal route (e.g., the IC route 44A) includes the internal circulation circuit (e.g., the IC circulation circuit 44A2) through which the liquid is circulated with respect to the treatment unit 20, and the internal supply circuit (e.g., the IC supply circuit 44A1) configured to supply the liquid to the internal circulation circuit, the external route (e.g., the EC route 44B) includes the external circulation circuit (e.g., the EC circulation circuit 44B2) through which the liquid is circulated with respect to the treatment unit 20, and the external supply circuit (e.g., the EC supply circuit 44B1) configured to supply the liquid to the external circulation circuit, and at the time of priming, a differential pressure is generated between the liquid circulating in the internal circulation circuit and the liquid circulating in the external circulation circuit. In accordance with such features, in the priming method, the amount of liquid used for priming can be suppressed, and the gas can be satisfactorily discharged from the hollow fibers 24.

Further, when the differential pressure is generated, supply of the liquid from the internal supply circuit (e.g., the IC supply circuit 44A1) and the external supply circuit (e.g., the EC supply circuit 44B1) is stopped, while on the other hand, a difference is brought about between the flow rate of the liquid circulating in the internal circulation circuit (e.g., the IC circulation circuit 44A2), and the flow rate of the liquid circulating in the external circulation circuit (e.g., the EC circulation circuit 44B2). In accordance with such features, in the priming method, it is possible to easily generate the differential pressure which enables the gas to be removed from the hollow fibers 24, while suppressing peeling of the coating 27 in the IC circulation circuit 44A2 and the EC circulation circuit 44B2.

At the time of priming, the differential pressure generating step of generating the differential pressure, and the discharging step of discharging the liquid and the gas from the internal circulation circuit (e.g., the IC circulation circuit 44A2) or the external circulation circuit (e.g., the EC circulation circuit 44B2) into the waste liquid route 44C are repeated. In accordance with this feature, in the priming method, the gas can be easily discharged from the hollow fibers 24 in the differential pressure generating step, and in the subsequent discharging step, the gas can be smoothly discharged together with the liquid into the waste liquid route 44C.

Further, the speed ratio between the flow rate of the liquid flowing through the internal circulation circuit (e.g., the IC circulation circuit 44A2) and the flow rate of the liquid flowing through the external circulation circuit (e.g., the EC circulation circuit 44B2) is set within a range of from 5 times to 15 times (e.g., faster). In accordance with this feature, in the priming method, an appropriate differential pressure can be generated between the internal pressure on the side of the inner cavities 24*a* of the hollow fibers 24 and the internal pressure on the outer side (e.g., the main space 26*a*) of the hollow fibers 24. As a result, at the time of priming, it is possible to more reliably remove the gas from the hollow fibers 24 while further suppressing peeling of the coating 27.

Further, when the differential pressure is generated, while the liquid is circulated in both the internal circulation circuit (e.g., the IC circulation circuit 44A2) and the external circulation circuit (e.g., the EC circulation circuit 44B2), the liquid is supplied from the internal supply circuit (e.g., the IC supply circuit 44A1) to the internal circulation circuit, or the liquid is supplied from the external supply circuit (e.g., the EC supply circuit 44B1) to the external circulation circuit. In the priming method, by the liquid being supplied from the internal supply circuit to the internal circulation circuit (or the liquid being supplied from the external supply circuit to the external circulation circuit), it is possible to easily increase the internal pressure of one from among the internal route and the external route. Thus, it becomes possible to easily obtain the differential pressure that enables the gas to be removed from the hollow fibers 24.

Further, the differential pressure is generated by increasing the internal pressure of the external route (e.g., the EC route 44B) with respect to the internal pressure of the internal route (e.g., the IC route 44A), and the gas is made to move from the hollow fibers 24 into the inner cavities 24*a*. In accordance with this feature, in the priming method, the gas in the hollow fibers 24 can be easily made to move into the inner cavities 24*a*, and can be discharged through the internal route.

Further, the differential pressure is generated by increasing the internal pressure of the internal route (e.g., the IC route 44A) with respect to the internal pressure of the external route (e.g., the EC route 44B), and the gas is made to move from the hollow fibers 24 into the internal space (e.g., the main space 26*a*). In accordance with this feature, in the priming method, the gas in the hollow fibers 24 can be easily made to move into the internal space, and can be discharged through the external route.

The treatment unit 20 is the bioreactor 21 configured to cause the cells to be adhered to the inner circumferential surfaces of the hollow fibers 24, and thereafter, supply the culture medium to the hollow fibers 24, and cause the cells to undergo propagation on the inner circumferential surfaces of the hollow fibers 24, and the priming method is carried out prior to supplying the liquid containing the cells to the hollow fibers 24. In accordance with such features, by executing the priming method, the bioreactor 21 can satisfactorily cause the cells to be propagated in the hollow fibers 24 from which the gas has been discharged from the hollow fibers 24.

Further, the second aspect of the present disclosure is characterized by the biological component treatment system 22 including the treatment unit 20 comprising the hollow fibers 24 on which the coating 27 is formed on the inner circumferential surfaces that constitute the inner cavities 24*a* thereof, and the container 26 having the internal space (the main space 26*a*) in which the hollow fibers 24 are accommodated, the biological component treatment system including the internal route (the IC route 44A) connected to the treatment unit 20 (e.g., fluidically connected to the treatment unit 20), and through which the liquid is allowed to flow in the inner cavities 24*a*, the external route (the EC route 44B) connected to the treatment unit 20 (e.g., fluidically connected to the treatment unit 20), and through which the liquid is allowed to flow in the internal space on the outer side of the hollow fibers 24, and the control unit 136 configured to control the flowing state of the liquid through the internal route and the external route, wherein the control unit 136, at a time of priming, while the liquid flows through both the internal route and the external route, causes the differential pressure to be generated between the liquid flowing through the inner cavities 24*a* and the liquid flowing through the internal space, and causes the gas to flow out from the hollow fibers 24. In the biological component treatment system 22, it is possible to easily and reliably discharge the gas from the hollow fibers 24.

What is claimed is:

1. A priming method for discharging a gas contained within hollow fibers by introducing a cleaning liquid into a treatment unit comprising:

the hollow fibers, the hollow fibers containing a coating that promotes seeding of cells and that is formed on inner circumferential surfaces that constitute inner cavities of the hollow fibers, and a container having an internal space in which the hollow fibers are disposed, wherein the treatment unit includes:

an internal route through which the cleaning liquid is allowed to flow in the inner cavities; and an external route through which the cleaning liquid is allowed to flow in the internal space on an outer side of the hollow fibers, the method comprising:

flowing the cleaning liquid through the internal route at a first flow rate and in a first flow direction;

while the cleaning liquid flows through the internal route at the first flow rate and in the first flow direction, flowing the cleaning liquid through the external route at a second flow rate, different from the first flow rate, and in a second flow direction, opposite the first flow direction, to generate a differential pressure between the internal route and the external route that forces the gas out of the hollow fibers toward either the internal route or the external route without peeling the coating from the inner circumferential surfaces; and discharging the cleaning liquid and the gas from the internal route or the external route into a waste liquid bag.

2. The priming method of claim 1, wherein the internal route includes an internal circulation circuit through which the cleaning liquid is circulated with respect to the treatment unit, and an internal supply circuit configured to supply the cleaning liquid to the internal circulation circuit, and wherein the external route includes an external circulation circuit through which the cleaning liquid is circulated with respect to the treatment unit, and an external supply circuit configured to supply the cleaning liquid to the external circulation circuit.

3. The priming method of claim 2, further comprising:

when the differential pressure is generated, stopping a supply of the cleaning liquid from the internal supply circuit and the external supply circuit.

4. The priming method of claim 2, wherein discharging the cleaning liquid and the gas from the internal circulation circuit or the external circulation circuit into the waste liquid bag comprises:

opening a first clamp within a waste liquid route that leads to the waste liquid bag;

closing or maintaining closure of a second clamp within the waste liquid route that leads to the waste liquid bag;

stopping first and second pumps of one of the internal circulation circuit or the external circulation circuit;

operating third and fourth pumps of the other one of the internal circulation circuit or the external circulation circuit to force the cleaning liquid and the gas into the waste liquid route; and rotating the container to a vertical position to discharge the cleaning liquid and the gas to the waste liquid bag via the opened first clamp within the waste liquid route.

5. The priming method of claim 1, wherein a ratio between the first flow rate and the second flow rate or a ratio between the second flow rate and the first flow rate is set within a range of 5:1 to 15:1.

6. The priming method of claim 2, further comprising:

when the differential pressure is generated and while the cleaning liquid is circulated in both the internal circulation circuit and the external circulation circuit, supplying the cleaning liquid from the internal supply circuit to the internal circulation circuit.

7. The priming method of claim 2, further comprising:

when the differential pressure is generated and while the cleaning liquid is circulated in both the internal circulation circuit and the external circulation circuit, supplying the cleaning liquid from the external supply circuit to the external circulation circuit.

8. The priming method of claim 1, wherein the differential pressure forces the gas to move from the hollow fibers into the inner cavities.

9. The priming method of claim 1, wherein the differential pressure forces the gas to move from the hollow fibers into the internal space.

10. The priming method of claim 1, wherein the priming method is performed before supplying a liquid containing cells to the hollow fibers, wherein, the treatment unit is a bioreactor, and wherein the method further comprises:

supplying the liquid containing the cells to the hollow fibers to allow the cells to be adhered to inner circumferential surfaces of the hollow fibers;

supplying a culture medium to the hollow fibers; and allowing the cells to undergo propagation on inner circumferential surfaces of the hollow fibers.

11. A biological component treatment system comprising:

a treatment unit comprising hollow fibers on which a coating that promotes seeding of cells and that is formed on inner circumferential surfaces that create inner cavities of the hollow fibers;

a container having an internal space in which the hollow fibers are disposed;

an internal route connected to the treatment unit, and through which a cleaning liquid is allowed to flow in the inner cavities;

an external route connected to the treatment unit, and through which the cleaning liquid is allowed to flow in the internal space on an outer side of the hollow fibers; and a control unit configured to control a flow of the cleaning liquid through the internal route and the external route such that:

the cleaning liquid flows through the internal route at a first flow rate and in a first flow direction;

while the cleaning liquid flows through the internal route at the first flow rate and in the first flow direction, the cleaning liquid flows through the external route at a second flow rate, different from the first flow rate, and in a second flow direction, opposite the first flow direction, to generate a differential pressure between the internal route and the external route that forces gas out of the hollow fibers toward either the internal route or the external route but without peeling the coating from the inner circumferential surfaces; and the cleaning liquid and the gas are discharged from the internal route or the external route into a waste liquid bag.

12. The biological component treatment system of claim 11, wherein the internal route includes an internal circulation circuit that circulates the cleaning liquid through the treatment unit and an internal supply circuit that supplies the cleaning liquid to the internal circulation circuit, and wherein the external route includes an external circulation circuit that circulates the cleaning liquid through the treatment unit and an external supply circuit that supplies the cleaning liquid to the external circulation circuit.

13. The biological component treatment system of claim 11, wherein a ratio between the second flow rate and the first flow rate is set within a range of 5:1 to 15:1.

14. The biological component treatment system of claim 12, the control unit is configured to, when the differential pressure is generated, stop a supply of the cleaning liquid from the internal supply circuit and the external supply circuit.

15. The biological component treatment system of claim 11, wherein a ratio between the first flow rate and the second flow rate is set within a range of 5:1 to 15:1.

16. A biological component treatment apparatus, comprising:

a bioreactor that includes hollow fibers with inner circumferential surfaces each coated with a coating that promotes seeding of cells to create respective inner cavities in the hollow fibers;

a container with an internal space housing the hollow fibers;

an internal route fluidically connected to the bioreactor and configured to permit a cleaning liquid to flow in the inner cavities of the hollow fibers;

an external route fluidically connected to the bioreactor and configured to permit the cleaning liquid to flow in the internal space on an outer side of the hollow fibers; and a control unit configured to control flow of the cleaning liquid through both the internal route and the external route such that:

the cleaning liquid flows through the internal route at a first flow rate and in a first flow direction;

while the cleaning liquid flows through the internal route at the first flow rate and in the first flow direction, the cleaning liquid flows through the external route at a second flow rate, different from the first flow rate, and in a second flow direction, opposite the first flow direction, to generate a differential pressure between the internal route and the external route that forces gas out of the hollow fibers toward either the internal route or the external route but without peeling the coating from the inner circumferential surfaces; and the cleaning liquid and the gas are discharged from the internal route or the external route into a waste liquid bag.

17. The biological component treatment apparatus of claim 16, wherein the internal route includes an internal circulation circuit that circulates the cleaning liquid through the bioreactor and an internal supply circuit that supplies the cleaning liquid to the internal circulation circuit, and wherein the external route includes an external circulation circuit that circulates the cleaning liquid through the bioreactor and an external supply circuit that supplies the cleaning liquid to the external circulation circuit.

18. The biological component treatment apparatus of claim 16, wherein a ratio between the second flow rate and the first flow rate is set within a range of 5:1 to 15:1.

19. The biological component treatment apparatus of claim 17, the control unit is configured to, when the differential pressure is generated, stop a supply of the cleaning liquid from the internal supply circuit and the external supply circuit.

20. The biological component treatment apparatus of claim 16, wherein a ratio between the first flow rate and the second flow rate of is set within a range of 5:1 to 15:1.

* * * * *